US009134314B2

(12) United States Patent
Markowitz et al.

(10) Patent No.: US 9,134,314 B2
(45) Date of Patent: Sep. 15, 2015

(54) METHODS FOR DIAGNOSING AND TREATING CANCERS

(75) Inventors: Sanford D. Markowitz, Pepper Pike, OH (US); Joseph Willis, Shaker Heights, OH (US); Dawn Dawson, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 932 days.

(21) Appl. No.: 12/676,817

(22) PCT Filed: Sep. 5, 2008

(86) PCT No.: PCT/US2008/010395
§ 371 (c)(1),
(2), (4) Date: Aug. 24, 2010

(87) PCT Pub. No.: WO2009/032292
PCT Pub. Date: Mar. 12, 2009

(65) Prior Publication Data
US 2011/0027283 A1      Feb. 3, 2011

Related U.S. Application Data

(60) Provisional application No. 60/967,665, filed on Sep. 6, 2007.

(51) Int. Cl.
*G01N 33/574* (2006.01)
*C12Q 1/68* (2006.01)
*G01N 33/68* (2006.01)

(52) U.S. Cl.
CPC ........ *G01N 33/57407* (2013.01); *C12Q 1/6886* (2013.01); *G01N 33/57415* (2013.01); *G01N 33/57423* (2013.01); *G01N 33/57434* (2013.01); *G01N 33/57438* (2013.01); *G01N 33/57442* (2013.01); *G01N 33/57446* (2013.01); *G01N 33/57449* (2013.01); *G01N 33/57488* (2013.01); *G01N 33/6893* (2013.01); *C12Q 2600/158* (2013.01); *G01N 2500/00* (2013.01); *G01N 2800/046* (2013.01)

(58) Field of Classification Search
None
See application file for complete search history.

(56) References Cited

U.S. PATENT DOCUMENTS

| | | |
|---|---|---|
| 7,081,516 B2 | 7/2006 | Markowitz |
| 7,118,912 B2 | 10/2006 | Markowitz |
| 8,268,568 B2 | 9/2012 | Markowitz |
| 2003/0077568 A1 | 4/2003 | Gish et al. |
| 2003/0232350 A1 | 12/2003 | Afar et al. |
| 2003/0235820 A1 | 12/2003 | Mack et al. |
| 2004/0002120 A1 | 1/2004 | Kekuda et al. |
| 2004/0005563 A1 | 1/2004 | Mack et al. |
| 2004/0038220 A1 | 2/2004 | Markowitz et al. |
| 2004/0038225 A1 | 2/2004 | Markowitz et al. |
| 2007/0014801 A1* | 1/2007 | Gish et al. ............... 424/155.1 |

FOREIGN PATENT DOCUMENTS

| | | |
|---|---|---|
| WO | WO 99/38881 | 8/1999 |
| WO | WO 01/22920 | 4/2001 |
| WO | WO 01/75067 | 10/2001 |
| WO | WO 01/90357 | 11/2001 |
| WO | WO 01/96523 | 12/2001 |
| WO | WO 02/00939 | 1/2002 |
| WO | WO 02/21996 | 3/2002 |
| WO | WO 02/30268 A2 | 4/2002 |
| WO | WO 02/50301 | 6/2002 |
| WO | WO 02/068677 | 9/2002 |
| WO | WO 02/086443 A2 | 10/2002 |
| WO | WO 02/102235 A2 | 12/2002 |
| WO | WO 03/012070 | 2/2003 |
| WO | WO 03/025138 | 3/2003 |
| WO | WO 03/042661 | 5/2003 |
| WO | WO 2004/018647 A2 | 3/2004 |
| WO | WO 2004/018648 A2 | 3/2004 |

OTHER PUBLICATIONS

Rubanyi, Molecular Aspects of Medecine 2001;22:113-142.*
Pai et al, Gene Therapy, 2006; 13:464-477.*
Ryther et al, Gene Therapy, 2005; 12:5-11.*
Gebauer et al., "O-Glucosylation and O-Fucosylation Occur Together in Close Proximity on the First Epidermal Growth Factor Repeat of AMACO (VWA2 Protein)*," The Journal of Biological Chemistry, vol. 283(26), pp. 17846-17854, XP-002508748 (2008).
Sengle Gerhard et al, "Identification and characterization of AMACO, a new member of the von Willebrand factor A-like domain protein superfamily with a regulated expression in the kidney," The Journal of Biological Chemistry, vol. 278(50), pp. 50240-50249 (2003).
Willis et al., "Colon cancer secreting protein-2 is expressed in a spectrum of common adenocarcinomas," Laboratory Investigation, vol. 88, No. Suppl.1, p. 140A, XP009110212 and 97th Annual Meeting of the United-States-and-Canadian-Academy-of-Pathology, Denver, CO Mar. 1-7, 2008; Abstract (2008).
Xin et al., "Colon Cancer Secreted Protein-2 (CCSP-2), A Novel Candidate Serological Marker of Colon Neoplasia," *Oncogene* 24:724-731 (2005).
Alon, U. et al. Broad patterns of gene expression revealed by clustering analysis of tumor and normal colon tissues probed by oligonucleotide arrays. PNAS 96, 745-6750 (Jun. 1999).
Bieller, A. et al. Isolation and Characterization of the Human Forkhead Gene FOXQ1. DNA Cell Biol. 20, 555-561 (2001).

(Continued)

*Primary Examiner* — Mark Halvorson
(74) *Attorney, Agent, or Firm* — Ropes & Gray LLP

(57) ABSTRACT

This disclosure provides methods and compositions for inhibiting immune responses. The disclosure also provides methods and compositions for inhibiting graft rejection and promoting or prolonging graft survival.

24 Claims, 10 Drawing Sheets

(56) References Cited

OTHER PUBLICATIONS

Bowie et al., "Deciphering the Message in Protein Sequences: Tolerance to Amino Acid Substitutions," Science, vol. 247, pp. 1306-1310 (1990).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111, pp. 2129-2138 (1990).
Chen et al., "Discordant Protein and mRNA Expression in Lung Adenocarcinomas", Molecular & Cellular Protemics, DOI 10.1074/mcp.M200008-MCP200:304-313(2002).
Critchfield, G.C., "The Future of DNA Diagnostics," Disease Markers, vol. 15 pp. 108-111 (1999).
Database EMBL, "*Homo sapiens* mRNA for KIAA1199 protein, partial cds," Database accession No. AB033025, Nov. 11, 1999.
De Plaen et al., "Structure, chromosomal localization, and expression of 12 genes of the MAGE family," Immunogenetics, vol. 40, pp. 360-369 (1994).
Deng, G. et al. Methylation of CpG in a Small Region of the hMLH1 Promoter Invariably Correlates with the Absence of Gene Expression. Cancer Res. 59, 2029-2033 (May 1, 1999).
Esteller, M. et al. Detection of Aberrant Promoter Hypermethylation of Tumor Suppressor Genes in Serum DNA from Non-Small Cell Lung Cancer Patients. Cancer Res. 59, 67-70 (Jan. 1, 1999).
GenBank Accession No. AAG41062 (Aug. 29, 2000).
GenBank Accession No. AI357412 (Jan. 6, 1999).
GenBank Accession No. AI590539 (Apr. 9, 1999).
GenBank Accession No. AI870708 (Jul. 21, 1999).
GenBank Accession No. AY007815 (Aug. 29, 2000).
GenBank Accession No. BAA92054 (Feb. 16, 2000).
GenBank Accession No. W07459 (Apr. 25, 1996).
GenBank Accession No. XM_061091 (Jul. 31, 2002).
Gray, Marion., "Clinical Use of Serum Prostate-Specific Antigen: a Review", Clin. Lab, 51:127-133(2005).
Guo et al., "Protein tolerance to random amino acid change," Proc. Natl. Acad. Sci. USA., vol. 101(25), pp. 9205-9210 (2004).
Hardy, R.G. et al. Aberrant P-cadherin expression is an early event in hyperplastic and dysplastic transformation in the colon. Gut 50, 513-519 (2002).
Herman, J.G. et al. Incidence and functional consequences of hMLH1 promoter hypermethylation in colorectal carcinoma. PNAS 95, 6870-6875 (Jun. 1998).
Hibi, K. et al. Molecular Detection of Genetic Alterations in the Serum of Colorectal Cancer Patients. Cancer Res. 58, 1405-1407 (Apr. 1, 1998).
Hong et al., "The Winged Helix/Forkhead Transcription Factor Foxq1 Regulates Differentiation of Hair in Satin Mice", Genesis 29:163-171(2001).
Kane, M.F. et al. Methylation of the hMLH1 Promoter Correlates with Lack of Expression of hMLH1 in Sporadic Colon Tumors and Mismatch Repair-defective Human Tumor Cell Lines. Cancer Res. 57, 808-811 (Mar. 1, 1997).
Kennel, David E., "Principles and Practices of Nucleic Acid Hybridization", Nucl. Acid Res. Mol. Biol. 11: 259(1971).
Kobayashi, A. et al. Molecular Cloning and Functional Characterization of a New Cap'n' Collar Family Transcription Factor Nrf3. J. Biol. Chem. 274, 6443-6452 (Mar. 5, 1999).
Lazar et al., "Transforming Growth Factor α: Mutation of Aspartic Acid 47 and Leucine 48 Results in Different Biological Activities," Molecular and Cellular Biology, vol. 8(3), pp. 1247-1252 (1988).
Liu et al., "Detection of Low Level HER-2/neu Gene Amplification in Prostate Cancer by Flourescence in Situ Hybridization", The Cancer Journal, 7(5):395-403(2001).
Markowitz, S. et al. Inactivation of the Type II TGF-$\beta$ Receptor in Colon Cancer Cells with Microsatellite Instability. Science 268, 1336-1338 (1995).
Michishita et al., "Upregulation of the KIAA1199 gene is associated with cellular mortality," Cancer Letters, vol. 239, pp. 71-77 (2006).
Radice, G.L. et al. Precocious Mammary Gland Development in P-Cadherin-deficient Mice. J. Cell Biol. 139, 1025-1032 (Nov. 17, 1997).
Rae et al., "Novel Association of a Diverse Range of Genes with Renal Cell Carcinoma as Identified by Differential Display," International Journal of Cancer, vol. 88, pp. 726-732 (200).
Roessler et al., "Identification of Nicotinamide N-Methyltransferase as a Novel Serum Tumor Marker for Colorectal Cancer," Clinical Cancer Research, vol. 11(18), pp. 6550-6557 (2005).
Roessler et al., "Identification of PSME3 as a Novel Serum Tumor Marker for Colorectal Cancer by Combining Two-dimensional Polyacrylamide Gel Electrophoresis with a Strictly Mass Spectrometry-based Approach for Data Analysis*," Molecular & Cellular Proteomics, vol. 5(11), pp. 2092-2101 (2006).
Scott, D.A. et al. Refining the DFNB7-DFNB11 deafness locus using intragenic polymorphisms in a novel gene, TMEM2. Gene 246, 265-274 (2000).
Shimoyama, Y. et al. Molecular Cloning of a Human Ca2+-dependent Cell-Cell Adhesion Molecule Homologous to Mouse Placental Cadherin: Its Low Expression in Human Placental Tissues. J. Cell Biol. 109, 1787-1794 (1989).
Sidransky et al., "Nucleic Acid-Based Methods for the Detection of Cancer," Science, vol. 278, pp. 1054-1058 (1997).
Skolnick et al., "From genes to protein structure and function: novel applications of computational approaches in the genomic era," Trends Biotechnol, vol. 18(1), pp. 34-39 (2000).
Srivastava et al., "Biomarkers for Early Detection of Colon Cancer," Clinical Cancer Research 7:1118-1126 (2001).
Takada et al., "Alteration of a Single Amino Acid in Peroxisome Proliferator-Activated Receptor—α (PPARα) Generates a PPARo Phenotype," Molecular Endocrinology, vol. 14(5), pp. 733-740 (2000).
Tockman et al., "Considerations in Bringing a Cancer Biomarker to Clinical Application," Cancer Research (Suppl.), vol. 52, pp. 2711s-2718s (1992).
Unigene Hs.157601, *Homo sapiens* transcribed sequences.
Veigl, M.L. et al. Biallelic inactivation of hMLH1 by epigenetic gene silencing, a novel mechanism causing human MSI cancers. PNAS 95, 8698-8702 (Jul. 1998).
Ward A. Milford, "Tumour Markers," Developmental Oncology, vol. 21, pp. 91-106 (1985).
Weber, G.F. The metastasis gene osteopontin: a candidate target for cancer therapy. Biochim. Biophys. Acta. 1552, 61-85 (2001).
Wines, M.E. et al. Identification of Mesoderm Development (mesd) Candidate Genes by Comparative Mapping and Genome Sequence Analysis. Genomics 88-98 (2001).
Wong, I.H.N. et al. Detection of Aberrant p16 Methylation in the Plasma and Serum of Liver Cancer Patients. Cancer Res. 59, 71-73 (Jan. 1, 1999).
Zhang, J.-S. et al. Keratin 23 (K23), a Novel Acidic Keratin, Is Highly Induced by Histone Deacetylase Inhibitors During Differentiation of Pancreatic Cancer Cells. Genes Chromosomes Cancer 30, 123-135 (2001).
Zolg et al., "How Industry Is Approaching the Search of New Diagnostic Markers and Biomarkers*," Molecular & Cellular Proteomics, vol. 3(4), pp. 345-354 (2004).

\* cited by examiner

LQEVHVSKETIGKISAASKMMWCSAAVDIMFLLDGSNSVGKGSFERSKHFAITVCDGLD
ISPERVRVGAFQFSSTPHLEFPLDSFSTQQEVKARIKRMVFKGGRTETELALKYLLHRG
LPGGRNASVPQILIIVTDGKSQGDVALPSKQLKERGVTVFAVGVRFPRWEELHALASEP
RGQHVLLAEQVEDATNGLFSTLSSSAICSSATPDCRVEAHPCEHRTLEMVREFAGNAPC
WRGSRRTLAVLAAHCPFYSWKRVFLTHPATCYRTTCPGPCDSQPCQNGGTCVPEGLDGY
QCLCPLAFGGEANCALKLSLECRVDLLFLLDSSAGTTLDGFLRAKVFVKRFVRAVLSED
SRARVGVATYSRELLVAVPVGEYQDVPDLVWSLDGIPFRGGPTLTGSALRQAAERGFGS
ATRTGQDRPRRVVVLLTESHSEDEVAGPARHARARELLLLGVGSEAVRAELEEITGSPK
HVMVYSDPQDLFNQIPELQGKLCSRQRPGCRTQALDLVFMLDTSASVGPENFAQMQSFV
RSCALQFEVNPDVTQVGLVVYGSQVQTAFGLDTKPTRAAMLRAISQAPYLGGVGSAGTA
LLHIYDKVMTVQRGARPGVPKAVVVLTGGRGAEDAAVPAQKLRNNGISVLVVGVGPVLS
EGLRRLAGPRDSLIHVAAYADLRYHQDVLIEWLCGEAKQPVNLCKPSPCMNEGSCVLQN
GSYRCKCRDGWEGPHCENRFLRRP

Fig. 1
Amino acid sequence of secreted ColoUp2 protein
(SEQ ID NO: 1)

GCCCCCTGGCCCGAGCCGCGCCCGGGTCTGTGAGTAGAGCCGCCCGGGCACCGAGCGCT
GGTCGCCGCTCTCCTTCCGTTATATCAACATGCCCCCTTTCCTGTTGCTGGAAGCCGTC
TGTGTTTTCCTGTTTTCCAGAGTGCCCCCATCTCTCCCTCTCCAGGAAGTCCATGTAAG
CAAAGAAACCATCGGGAAGATTTCAGCTGCCAGCAAAATGATGTGGTGCTCGGCTGCAG
TGGACATCATGTTTCTGTTAGATGGGTCTAACAGCGTCGGGAAAGGGAGCTTTGAAAGG
TCCAAGCACTTTGCCATCACAGTCTGTGACGGTCTGGACATCAGCCCCGAGAGGGTCAG
AGTGGGAGCATTCCAGTTCAGTTCCACTCCTCATCTGGAATTCCCCTTGGATTCATTTT
CAACCCAACAGGAAGTGAAGGCAAGAATCAAGAGGATGGTTTTCAAAGGAGGGCGCACG
GAGACGGAACTTGCTCTGAAATACCTTCTGCACAGAGGGTTGCCTGGAGGCAGAAATGC
TTCTGTGCCCCAGATCCTCATCATCGTCACTGATGGGAAGTCCCAGGGGGATGTGGCAC
TGCCATCCAAGCAGCTGAAGGAAAGGGGTGTCACTGTGTTTGCTGTGGGGGTCAGGTTT
CCCAGGTGGGAGGAGCTGCATGCACTGGCCAGCGAGCCTAGAGGGCAGCACGTGCTGTT
GGCTGAGCAGGTGGAGGATGCCACCAACGGCCTCTTCAGCACCCTCAGCAGCTCGGCCA
TCTGCTCCAGCGCCACGCCAGACTGCAGGGTCGAGGCTCACCCCTGTGAGCACAGGACG
CTGGAGATGGTCCGGGAGTTCGCTGGCAATGCCCCATGCTGGAGAGGATCGCGGCGGAC
CCTTGCGGTGCTGGCTGCACACTGTCCCTTCTACAGCTGGAAGAGAGTGTTCCTAACCC
ACCCTGCCACCTGCTACAGGACCACCTGCCCAGGCCCCTGTGACTCGCAGCCCTGCCAG
AATGGAGGCACATGTGTTCCAGAAGGACTGGACGGCTACCAGTGCCTCTGCCCGCTGGC
CTTTGGAGGGGAGGCTAACTGTGCCCTGAAGCTGAGCCTGGAATGCAGGGTCGACCTCC
TCTTCCTGCTGGACAGCTCTGCGGGCACCACTCTGGACGGCTTCCTGCGGGCCAAAGTC
TTCGTGAAGCGGTTTGTGCGGGCCGTGCTGAGCGAGGACTCTCGGGCCCGAGTGGGTGT
GGCCACATACAGCAGGGAGCTGCTGGTGGCGGTGCCTGTGGGGGAGTACCAGGATGTGC
CTGACCTGGTCTGGAGCCTCGATGGCATTCCCTTCCGTGGTGGCCCCACCCTGACGGGC
AGTGCCTTGCGGCAGGCGGCAGAGCGTGGCTTCGGGAGCGCCACCAGGACAGGCCAGGA
CCGGCCACGTAGAGTGGTGGTTTTGCTCACTGAGTCACACTCCGAGGATGAGGTTGCGG
GCCCAGCGCGTCACGCAAGGGCGCGAGAGCTGCTCCTGCTGGGTGTAGGCAGTGAGGCC
GTGCGGGCAGAGCTGGAGGAGATCACAGGCAGCCCAAAGCATGTGATGGTCTACTCGGA
TCCTCAGGATCTGTTCAACCAAATCCCTGAGCTGCAGGGGAAGCTGTGCAGCCGGCAGC
GGCCAGGGTGCCGGACACAAGCCCTGGACCTCGTCTTCATGTTGGACACCTCTGCCTCA
GTAGGGCCCGAGAATTTTGCTCAGATGCAGAGCTTTGTGAGAAGCTGTGCCCTCCAGTT
TGAGGTGAACCCTGACGTGACACAGGTCGGCCTGGTGGTGTATGGCAGCCAGGTGCAGA
CTGCCTTCGGGCTGGACACCAAACCCACCCGGGCTGCGATGCTGCGGGCCATTAGCCAG
GCCCCCTACCTAGGTGGGGTGGGCTCAGCCGGCACCGCCCTGCTGCACATCTATGACAA
AGTGATGACCGTCCAGAGGGGTGCCCGGCCTGGTGTCCCCAAAGCTGTGGTGGTGCTCA
CAGGCGGGAGAGGCGCAGAGGATGCAGCCGTTCCTGCCCAGAAGCTGAGGAACAATGGC
ATCTCTGTCTTGGTCGTGGGCGTGGGGCCTGTCCTAAGTGAGGGTCTGCGGAGGCTTGC
AGGTCCCCGGGATTCCCTGATCCACGTGGCAGCTTACGCCGACCTGCGGTACCACCAGG
ACGTGCTCATTGAGTGGCTGTGTGGAGAAGCCAAGCAGCCAGTCAACCTCTGCAAACCC
AGCCCGTGCATGAATGAGGGCAGCTGCGTCCTGCAGAATGGGAGCTACCGCTGCAAGTG
TCGGGATGGCTGGGAGGGCCCCCACTGCGAGAACCGATTCTTGAGACGCCCTGAGGCA
CATGGCTCCCGTGCAGGAGGGCAGCAGCCGTACCCCTCCCAGCAACTACAGAGAAGGCC
TGGGCACTGAAATGGTGCCTACCTTCTGGAATGTCTGTGCCCCAGGTCCTTAGAATGTC
TGCTTCCCGCCGTGGCCAGGACCACTATTCTCACTGAGGGAGGAGGATGTCCCAACTGC
AGCCATGCTGCTTAGAGACAAGAAAGCAGCTGATGTCACCCACAAACGATGTTGTTGAA
AAGTTTTGATGTGTAAGTAAATACCCACTTTCTGTACCTGCTGTGCCTTGTTGAGGCTA

Fig. 2
Nucleic acid sequence of ColoUp2
(SEQ ID NO: 2)

```
TGTCATCTGCCACCTTTCCCTTGAGGATAAACAAGGGGTCCTGAAGACTTAAATTTAGC
GGCCTGACGTTCCTTTGCACACAATCAATGCTCGCCAGAATGTTGTTGACACAGTAATG
CCCAGCAGAGGCCTTTACTAGAGCATCCTTTGGACGG
```

Fig. 2 continued.
Nucleic acid sequence of ColoUp2
(SEQ ID NO: 2)

```
MPPFLLLEAVCVFLFSRVPPSLPLQEVHVSKETIGKISAASKMMWCSAAVDIMFLLDGS
NSVGKGSFERSKHFAITVCDGLDISPERVRVGAFQFSSTPHLEFPLDSFSTQQEVKARI
KRMVFKGGRTETELALKYLLHRGLPGGRNASVPQILIIVTDGKSQGDVALPSKQLKERG
VTVFAVGVRFPRWEELHALASEPRGQHVLLAEQVEDATNGLFSTLSSSAICSSATPDCR
VEAHPCEHRTLEMVREFAGNAPCWRGSRRTLAVLAAHCPFYSWKRVFLTHPATCYRTTC
PGPCDSQPCQNGGTCVPEGLDGYQCLCPLAFGGEANCALKLSLECRVDLLFLLDSSAGT
TLDGFLRAKVFVKRFVRAVLSEDSRARVGVATYSRELLVAVPVGEYQDVPDLVWSLDGI
PFRGGPTLTGSALRQAAERGFGSATRTGQDRPRRVVVLLTESHSEDEVAGPARHARARE
LLLLGVGSEAVRAELEEITGSPKHVMVYSDPQDLFNQIPELQGKLCSRQRPGCRTQALD
LVFMLDTSASVGPENFAQMQSFVRSCALQFEVNPDVTQVGLVVYGSQVQTAFGLDTKPT
RAAMLRAISQAPYLGGVGSAGTALLHIYDKVMTVQRGARPGVPKAVVVLTGGRGAEDAA
VPAQKLRNNGISVLVVGVGPVLSEGLRRLAGPRDSLIHVAAYADLRYHQDVLIEWLCGE
AKQPVNLCKPSPCMNEGSCVLQNGSYRCKCRDGWEGPHCENRFLRRP
```

Fig. 3
Amino acid sequence of full-length ColoUp2 protein
(SEQ ID NO: 3)

AVLAAHCPFYSWKRVFLTHPATCYRTTCPFPPCDSQPCQNGGTCVPEGLDGYQCL
CPLAFGGEANCALKLSLECRVDLLFLLDSSAGTLDGFLRAKVFVRRFVRAVVLSE
DSRARVGVATYSRELLVAVPVGEYQDVPDLVWSLDGIPFRGGPTLTGSALRQAA
ERGFGSATRTGQDRPRRVVVLLTESHSEDEVAGPARHARARELLLLGVGSWAVR
AELEEITGSPKHVMVYSDPQDLFNQIPELQGKLCSRQRPGCRTQALDLVFMLDTS
ASVGPENFAQMQSFVRSCALQFEVVNPDVTQVGLVVYGSQVQTFFGLDTKPTRA
AMLRAISQAPYLGGVGSAGTALLHIYDKVMTVQRGARPGVPKAVVVLTGGRGA
EDAAVPAQKLRNNGISVLVVGVGPLSEGLRRLAGPRDSLIHVAAYADLRYHQD
VLIEWLCGEAKQPVNLCKPSPCMNEGSCVLQNGSYRCKCRDGWEGPHCENRFL
RRP

Fig. 7
Amino Acid Sequence of a Secreted C-terminal Portion of ColoUp2
(SEQ ID NO: 4)

METHODS FOR DIAGNOSING AND TREATING CANCERS

RELATED APPLICATIONS

This patent application is a U.S. national stage application filed under 35 U.S.C. §371 of International Application PCT/US2008/010395, filed Sep. 5, 2008, which claims the benefit of priority of U.S. Provisional Application No. 60/967,665 filed Sep. 6, 2007, the disclosures of which are incorporated herein by reference in their entirety. International Application No. PCT/US2008/010395 was published under PCT Article 21(2) in English.

FUNDING

Work described herein was funded, in part, by grant numbers U01 CA-88130 and RO1 CA120237 from the National Institutes of Health. The United States government has certain rights in the invention.

SEQUENCE LISTING

The instant application contains a Sequence Listing which has been submitted via EFS-Web and is hereby incorporated by reference in its entirety. Said ASCII copy, created on Mar. 5, 2010, is named CWRU014301.txt, and is 21,178 bytes in size.

BACKGROUND

Modern molecular biology has made it possible to identify proteins and nucleic acids that are specifically associated with certain physiological states. Improved systems for identifying high quality candidate molecular markers in large volumes of gene expression data may help to unlock the power of such tools and increase the likelihood of identifying a molecular marker for cancers. Effective molecular markers for cancers could potentially revolutionize the diagnosis, management and overall health impact of cancers. In addition, molecular markers may be used in screening for, generating and targeting therapeutic agents for cancers. Thus, there remains a need for novel molecular markers for detecting cancers and therapeutic agents in treating cancers.

SUMMARY OF THE INVENTION

In one aspect, this application provides ColoUp2 (also referred to as colon cancer secreted protein-2 (CCSP2)) as a molecular marker that is useful in the detection or diagnosis of neoplasias including cancers or precancers. In certain embodiments, molecular markers described in the application are helpful in distinguishing normal subjects from those who are likely to develop or likely to harbor a neoplasia. In other aspects, the invention provides molecular markers that may be useful in distinguishing subjects who are either normal or precancerous from those who have cancers. In another embodiment, the application provides markers that help in staging cancers in patients. In certain specific embodiments, the application contemplates the use of the molecular markers described herein for the detection, diagnosis, and staging of a neoplasia of a tissue type selected from endometrium, kidney, lung, stomach, pancreas, breast, prostate, ovary, uterus, and thyroid. In certain embodiments, the molecular markers disclosed herein may be used for identifying or targeting anti-neoplastic agents directed against neoplasias.

In one aspect, the application provides a method of screening a subject for a condition associated with increased levels of ColoUp2 by detecting in a biological sample an amount of ColoUp2 and comparing the amount of ColoUp2 found in the subject to one or more of the following: a predetermined standard, the amount of ColoUp2 detected in a normal sample from the subject, the subject's historical baseline level of ColoUp2, or the ColoUp2 level detected in a different, normal subject (a control subject). Detection of a level of ColoUp2 in the subject that is greater than that of the predetermined standard or that is increased from a subject's past baseline is indicative of a condition such as neoplasias. In certain aspects, an increase in the amount of ColoUp2 as compared to the subject's historical baseline would be indicative of a new neoplasia, or progression of an existing neoplasia. Similarly, a decrease in the amount of ColoUp2 as compared to the subject's historical baseline would be indicative of regression on an existing neoplasia. Exemplary neoplasias may be of a tissue type selected from endometrium, kidney, lung, stomach, pancreas, breast, prostate, ovary, uterus, and thyroid.

In yet another aspect, the application provides a method of determining whether a subject is likely to develop a neoplasia (cancer or precancer) or is more likely to harbor a neoplasia by detecting the presence or absence of the molecular markers as set forth in any of SEQ ID NOs: 1 and 3-4. Detection of these markers is also helpful in staging the neoplasia. In yet another aspect, the application provides markers that are useful in distinguishing normal and precancerous subjects from those subjects having a cancer. In certain embodiments, the application contemplates determining the levels of a ColoUp2 polypeptide. Optionally, the ColoUp2 polypeptide is a secreted polypeptide.

In certain embodiments, a secreted ColoUp2 polypeptide is selected from: a) a secreted polypeptide produced by the expression of a nucleic acid that is at least 95% identical to the nucleic acid sequence of SEQ ID NO: 2; b) a secreted polypeptide produced by the expression of a nucleic acid that is a naturally occurring variant of SEQ ID NO: 2; c) a secreted polypeptide produced by the expression of a nucleic acid that hybridizes under stringent conditions to a nucleic acid sequence of SEQ ID NO: 2; d) a secreted polypeptide having a sequence that is at least 95% identical to the amino acid sequence of SEQ ID NO: 1; and e) a secreted polypeptide having a sequence that is at least 95% identical to the amino acid sequence of SEQ ID NO: 4. Optionally, the secreted ColoUp2 polypeptide is produced by the expression of a nucleic acid having the sequence of SEQ ID NO: 2, and preferably the secreted ColoUp2 polypeptide is produced by the expression of a nucleic acid sequence that is at least 98%, 99% or 100% identical to the nucleic acid sequence of SEQ ID NO: 2. In certain embodiments, the secreted ColoUp2 polypeptide has an amino acid sequence that is at least 98%, 99% or 100% identical to an amino acid sequence selected from SEQ ID NO: 1 and SEQ ID NO: 4.

In certain aspect, the invention provides an immunoassay for determining the presence of any one of the polypeptides having an amino acid sequence as set forth in SEQ ID NOs: 1 and 3-4 in a biological sample. The method includes obtaining a biological sample and contacting the sample with an antibody specific for a polypeptide having an amino acid sequence as set forth in SEQ ID NOs: 1 and 3-4 and detecting the binding of the antibody.

In some aspects, the application provides methods for the detection of a molecular marker in a biological sample such as blood, including blood fractions such as serum or plasma. For instance, the blood sample obtained from a patient may be further processed such as by fractionation to obtain blood serum, and the serum may then be enriched for certain polypeptides. The serum so enriched is then contacted with an antibody that is reactive with an epitope of the desired marker polypeptide.

In yet another embodiment, the application provides methods for determining the appropriate therapeutic protocol for a subject. For example, detection of a neoplasia provides the treating physician valuable information in determining whether intensive or invasive protocols such as surgery or chemotherapy would be needed for effective diagnosis or treatment. Such detection would be helpful not only for patients not previously diagnosed with a neoplasia but also in those cases where a patient has previously received or is currently receiving therapy for cancer, the presence or absence or a change in the level of the molecular markers (e.g., ColoUp2) set forth herein may be indicative that the subject is likely to have a relapse or a progressive, or a persistent a cancer.

In yet other embodiments, the application provides a kit for detecting neoplasias in a biological sample, Such kits include one or more antibodies that are capable of interacting with an epitope specified by one of SEQ ID NOs: 1 and 3-4. In more preferred embodiments, the antibodies may be detectably labeled, such as for example with an enzyme, a fluorescent substance, a chemiluminescent substance, a chromophore, a radioactive isotope or a complexing agent.

In certain aspects, the application provides methods for inhibiting the growth or proliferation of a neoplasia in a subject, the method comprising administering to the subject an agent that decreases the amount of a ColoUp2 polypeptide present in or produced by the neoplasia. Optionally, the polypeptide is a secreted polypeptide (e.g., SEQ ID NO: 1 or 4). Optionally, the agent is an siRNA probe (or an RNAi construct) that hybridizes to an mRNA encoding a ColoUp2 polypeptide. In preferred embodiments, the siRNA probe hybridizes to a nucleic acid that is at least 90%, 95%, 98%, 99% or 100% identical to a nucleic acid sequence of SEQ ID NO: 2. Optionally, the agent is an antisense probe that hybridizes to a nucleic acid encoding a ColoUp2 polypeptide. In preferred embodiments, the antisense probe hybridizes to a nucleic acid that is at least 90%, 95%, 98%, 99% or 100% identical to a nucleic acid sequence of SEQ ID NO: 2. In certain embodiments, the agent comprises a nucleic acid vector that causes the production of a siRNA or an antisense probe that hybridizes to a nucleic acid encoding a ColoUp2 polypeptide. Exemplary neoplasias may be of a tissue type selected from endometrium, kidney, lung, stomach, pancreas, breast, prostate, ovary, uterus, and thyroid.

In certain aspects, the application provides a method for inhibiting the growth or proliferation of a cell of a neoplasia in a subject, the method comprising administering to the subject an agent that binds to and antagonizes a ColoUp2 polypeptide (e.g., a polypeptide selected from SEQ ID NOs: 1 and 3-4). In some embodiments, the agent comprises an antibody that binds to a ColoUp2 polypeptide. Optionally, the antibody is a monoclonal antibody, a polyclonal antibody or a single chain antibody. Optionally, the antibody is a humanized antibody. In certain embodiments, the agent is a small molecule that binds to a ColoUp2 polypeptide, and preferably a small molecule that inhibits an activity of a ColoUp2 polypeptide. For example, an agent may inhibit receptor binding (which may be assayed as cell surface binding) by a secreted ColoUp2 polypeptide (e.g., SEQ ID NO: 1 or 4).

In certain aspects, molecular markers of neoplasias may be used to target therapeutic agents to cells of a neoplasia. In certain embodiments, a therapeutic agent that is targeted to a neoplasia comprises a targeting moiety and an active moiety, wherein the targeting moiety binds to a ColoUp2 polypeptide and wherein the active moiety facilitates the killing or growth inhibition of a cell of a neoplasia. Optionally, the targeting moiety comprises an antibody. In preferred embodiments, the antibody binds to a polypeptide selected from SEQ ID NOs: 1 and 3-4. Optionally, the antibody is selected from a monoclonal antibody, a polyclonal antibody, a single chain antibody. In certain embodiments, the antibody is a humanized antibody. The active moiety may be, for example, a toxin, a chemotherapeutic agent, or an agent that sensitizes the cell to a chemotherapeutic agent or radiation. Exemplary neoplasias may be of a tissue type selected from endometrium, kidney, lung, stomach, pancreas, breast, prostate, ovary, uterus, and thyroid.

In certain embodiments, the application provides methods of identifying a candidate agent for treating cancers, the method comprising: identifying a candidate agent that binds to and/or inhibits an activity of a ColoUp2 polypeptide. In certain embodiments, the method may further comprise testing the candidate agent for anti-neoplastic effects on a cell of a neoplasia or a cell line derived from a neoplasia. The method may further comprise testing the candidate agent for anti-neoplastic effects on a mouse xenograft comprising cells of a human cancer or cells of a cell line derived from a cancer cell line. The candidate agent may be essentially any molecule or complex material of interest, including, for example, a siRNA probe, an antisense probe, an antibody and a small molecule.

In certain embodiments, the application provides use of an agent which reduces expression of the ColoUp2 gene or reduce activity of a ColoUp2 polypeptide in the manufacture of a medicament for treating a neoplasia in a subject. Exemplary neoplasias may be of a tissue type selected from endometrium, kidney, lung, stomach, pancreas, breast, prostate, ovary, uterus, and thyroid.

The embodiments and practices of the present invention, other embodiments, and their features and characteristics, will be apparent from the description, figures and claims that follow, with all of the claims hereby being incorporated by this reference into this Summary.

BRIEF DESCRIPTION OF THE DRAWINGS

FIG. 1 shows the amino acid sequence (SEQ ID NO: 1) of secreted ColoUp2 protein.

FIG. 2 shows the nucleic acid sequence (SEQ ID NO: 2) of ColoUp2.

FIG. 3 shows the amino acid sequence (SEQ ID NO: 3) of full-length ColoUp2 protein.

FIG. 6 shows, in the upper panel, the purification of ColoUp2 protein. Shown is a Coomassie blue staining of 250 ng (lane 2a) and 500 ng (lane 3a) of a purified ColoUp2 protein preparation. Size markers are in lane 1a.

FIG. 7 shows the amino acid sequence (SEQ ID NO: 4) of the approximately 55 kDa C-terminal fragment of ColoUp2 that is a prominent secreted and serum form of ColoUp2.

DETAILED DESCRIPTION

1. Definitions

Figure 4:
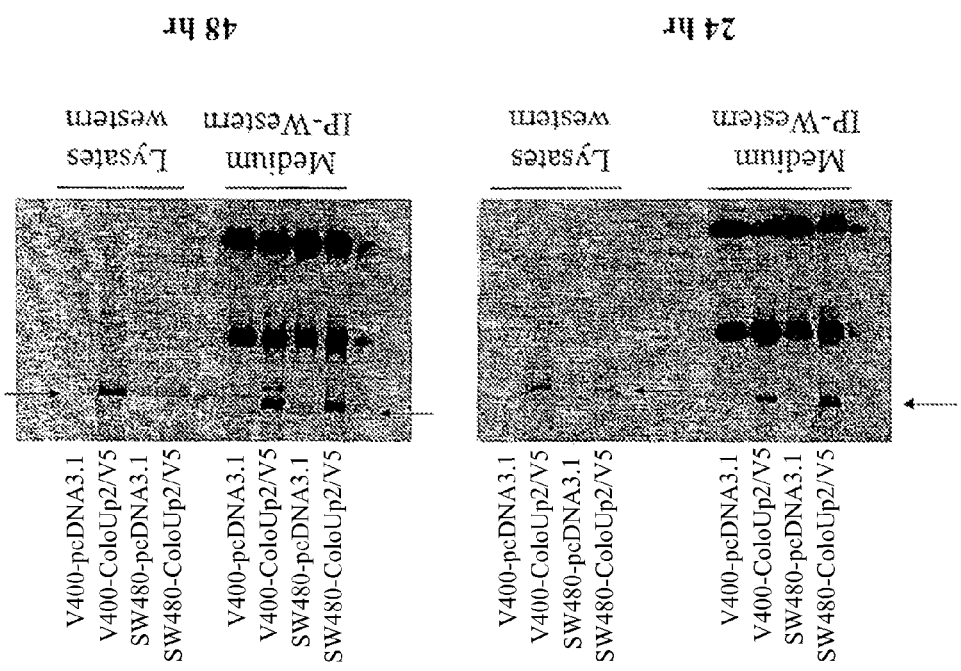
FIG. 4 shows detection of V5 epitope-tagged ColoUp2 protein levels in transfected SW480 cells and Vaco400 cells (24 hours and 48 hours after transfection). Expression of epitope-tagged ColoUp2 protein in transfected cells by Western blot (right panel), and secretion of epitope-tagged ColoUp2 protein in growth media by serial immunoprecipitation and Western blot (left panel).

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies.

The term "ColoUp2" is used to refer to a nucleic acid encoding a ColoUp2 protein or a ColoUp2 protein itself, as well as distinguishable fragments of such nucleic acids and proteins, longer nucleic acids and polypeptides that comprise distinguishable fragments or full length nucleic acids or polypeptides, and variants thereof. Variants include polypeptides that are at least 90% identical to the human ColoUp2 protein sequence referred to in the application, and nucleic acids encoding such variant polypeptides. In addition, variants include different post-translational modifications, such as glycosylations, methylations, etc. Particularly preferred variants include any naturally occurring variants, such as allelic differences, mutations that occur in a neoplasia and secreted or processed forms. The terms "variants" and "fragments" are overlapping.

As used herein, the phrase "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The term "detection" is used herein to refer to any process of observing a marker, in a biological sample, whether or not the marker is actually detected. In other words, the act of probing a sample for a marker is a "detection" even if the marker is determined to be not present or below the level of sensitivity. Detection may be a quantitative, semi-quantitative or non-quantitative observation.

The terms "healthy", "normal" and "non-neoplastic" are used interchangeably herein to refer to a subject or particular cell or tissue that is devoid (at least to the limit of detection) of a disease condition, such as a neoplasia, that is associated with increased expression of a ColoUp2 gene.

The term "including" is used herein to mean, and is used interchangeably with, the phrase "including but not limited to".

As used herein, the term "nucleic acid" refers to polynucleotides such as deoxyribonucleic acid (DNA), and, where appropriate, ribonucleic acid (RNA). The term should also be understood to include analogs of either RNA or DNA made from nucleotide analogs, and, as applicable to the embodiment being described, single-stranded (such as sense or antisense) and double-stranded polynucleotides.

The term "or" is used herein to mean, and is used interchangeably with, the term "and/or", unless context clearly indicates otherwise.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

The terms "polypeptide" and "protein" are used interchangeably herein.

The term "purified protein" refers to a preparation of a protein or proteins which are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

A "recombinant nucleic acid" is any nucleic acid that has been placed adjacent to another nucleic acid by recombinant DNA techniques. A "recombinant nucleic acid" also includes any nucleic acid that has been placed next to a second nucleic acid by a laboratory genetic technique such as, for example, transformation and integration, transposon hopping or viral insertion. In general, a recombined nucleic acid is not naturally located adjacent to the second nucleic acid.

The term "recombinant protein" refers to a protein that is produced by expression from a recombinant nucleic acid.

A "sample" includes any material that is obtained or prepared for detection of a molecular marker, or any material that is contacted with a detection reagent or detection device for the purpose of detecting a molecular marker.

A "subject" is any organism of interest, generally a mammalian subject, such as a mouse, and preferably a human subject.

2. Overview

In certain aspects, the invention relates to methods for determining whether a subject is likely or unlikely to have a neoplasia (e.g., tumor, cancer, and precancer) and markers that may be used to make such determination and to selected and/or target anti-neoplastic therapeutic agents. In other aspects, the invention relates to methods for determining whether a patient is likely or unlikely to have a neoplasia in tissues including, but is not limited to, stomach, pancreas, lung, breast, uterus, ovary, kidney, thyroid, prostate, and endometrium. In further aspects, the invention relates to methods for monitoring a neoplasia in a subject. In further aspects, the invention relates to methods for staging a subject's neoplasia. A neoplasia includes any cancerous or precancerous growth located in or derived from any tissue.

Early detection of cancers, coupled with appropriate intervention, is important for increasing patient survival rates. In addition, patients who receive surgical or pharmaceutical therapy for cancers may experience a relapse and it would be advantageous to have an alternative system for determining whether such patients have a recurrent or relapsed cancer. As an example, a cancer diagnostic system would facilitate monitoring an increase, decrease or persistence of a cancer in a patient known to have a cancer. A patient undergoing chemotherapy may be monitored to assess the effectiveness of the therapy.

Accordingly, in certain embodiments, the invention provides molecular markers (e.g., ColoUp2) that distinguish between cells that are not part of a neoplasia (e.g., cancer or precancer), referred to herein as "healthy cells", and cells that are part of a neoplasia, referred to herein as "neoplasia cells". For example, certain molecular markers, including ColoUp2, are expressed at significantly higher levels in cancer cell lines or tissues (e.g., stomach, pancreas, lung, breast, uterus, ovary, kidney, thyroid, prostate, and endometrium). Optionally, molecular markers of the invention which distinguish between healthy cells and cells of a neoplasia can be used for screening apparently healthy patients to determine whether the patient is at increased risk for (predisposed to) developing a cancer. Furthermore, preferred molecular markers are those that are actually present in the serum of an animal having a neoplasia, and in general, a secreted protein will generally occur in the serum if it is secreted from a cell contacting a blood vessel, or a compartment in diffusional contact with a blood vessel.

In certain specific embodiments, the invention provides methods for using the ColoUp2 molecular marker for determining whether a patient has or does not have a condition characterized by increased expression of ColoUp2 nucleic acids or proteins described herein. In certain embodiments, the invention provides methods for determining whether a patient is or is not likely to have a neoplasia. In further embodiments, the invention provides methods for determining whether the patient is having a relapse or determining whether a patient's neoplasia is responding to treatment.

In certain embodiments, a preferred molecular marker for use in a diagnostic test that employs a body fluid sample, such as a blood or urine sample, or an excreted sample material, such as stool, is a secreted protein, such as the secreted portion of a ColoUp2 protein. In certain embodiments, a preferred molecular marker for use in a diagnostic test to distinguish subjects likely to have a neoplasia (e.g., cancer or precancer) from those not likely to have a neoplasia is a gene product of the ColoUp2 gene. Examples of suitable gene products include proteins, both secreted and not secreted and transcripts. In embodiments employing proteins that are secreted, such as ColoUp2, a preferred embodiment of the diagnostic test is a test for the presence of the protein in a body fluid, such as urine or blood or an excreted material, such as stool. It should be noted, however, that intracellular protein may be present in a body fluid if there is significant cell lysis or through some other process. Likewise, secreted proteins are likely to be adherent, even if at a relatively low level, to the cells in which they were produced.

In certain aspects, the disclosure relates to ColoUp2 as a diagnostic marker and therapeutic target for cancers. The ColoUp2 nucleic acid sequence encodes a full-length protein of 755 amino acids. The application also discloses certain polymorphisms that have been observed, for example at nucleotide 113 GCC→ACC (Ala-Thr); nt 480 GAA→GGA (Glu-Gly); and at nt 2220 CAG→CGG (Gln-Arg). The sequence of ColoUp2 protein is similar to that of alpha 3 type VI collagen, isoform 2 precursor. In addition, a few domains are identified in the ColoUp2 protein such as a von Willebrand factor type A domain (vWF) and an EGF-like domain. The vWF domain is found in various plasma proteins such as some complement factors, the integrins, certain collagen, and other extracellular proteins. Proteins with vWF domains participate in numerous biological events which involve interaction with a large array of ligands, for example, cell adhesion, migration, homing, pattern formation, and signal transduction. The EGF-like domain consisting of about 30-40 amino acid residues has been found many proteins. The functional significance of EGF domains is not yet clear. However, a common feature is that these EGF-like repeats are found in the extracellular domain of membrane-bound proteins or in proteins known to be secreted.

As demonstrated herein, ColoUp2 is secreted from both the apical and basolateral surfaces of intestinal cells, and can be found in the blood in two different forms, a full-length secreted form and a C-terminal fragment (approximately 55 kDa).

In certain embodiments, the application provides isolated, purified or recombinant ColoUp2 nucleic acids. In certain embodiments, such nucleic acids may encode a complete or partial ColoUp2 polypeptide or such nucleic acids may also be probes or primers useful for methods involving detection or amplification of ColoUp2 nucleic acids. In certain embodiments, a ColoUp2 nucleic acid is single-stranded or double-stranded and composed of natural nucleic acids, nucleotide analogs, or mixtures thereof. In certain embodiments, the application provides isolated, purified or recombinant nucleic acids comprising a nucleic acid sequence that is at least 90% identical to a nucleic acid sequence of SEQ ID NO: 2, or a complement thereof, and optionally at least 95%, 97%, 98%, 99%, 99.3%, 99.5%, 99.7% or 100% identical to a nucleic acid of SEQ ID NO: 2, or a complement thereof. In certain preferred embodiments, the application provides a isolated, purified or recombinant nucleic acids comprising a nucleic acid sequence that is at least 90%, 95%, 97%, 98%, 99%, 99.3%, 99.5%, 99.7% or 100% identical to a nucleic acid of SEQ ID NO: 2, or a complement thereof. In certain embodiments, the application provides isolated, purified or recombinant nucleic acids comprising a nucleic acid sequence that encodes a polypeptide that is at least 90% identical to an amino acid sequence of any of SEQ ID NOs: 1 or 3-4, or a complement thereof, and optionally at least 95%, 97%, 98%, 99%, 99.3%, 99.5%, 99.7% or 100% identical to an amino acid sequence of any of SEQ ID NOs: 1 or 3-4, or a complement thereof.

In further embodiments, the application provides expression constructs, vectors and cells comprising a ColoUp2 nucleic acid. Expression constructs are nucleic acid constructs that are designed to permit expression of an expressible nucleic acid (e.g., a ColoUp2 nucleic acid) in a suitable cell type or in vitro expression system. A variety of expression construct systems are, in view of this specification, well known in the art, and such systems generally include a promoter that is operably linked to the expressible nucleic acid. The promoter may be a constitutive promoter, as in the case of many viral promoters, or the promoter may be a conditional promoter, as in the case of the prokaryotic lacI-repressible, IPTG-inducible promoter and as in the case of the eukaryotic tetracycline-inducible promoter. Vectors refer to any nucleic acid that is capable of transporting another nucleic acid to which it has been linked between different cells or viruses. One type of vector is an episome, i.e., a nucleic acid capable of extra-chromosomal replication, such as a plasmid. Episome-type vectors typically carry an origin of replication that directs replication of the vector in a host cell. Another type of vector is an integrative vector that is designed to recombine with the genetic material of a host cell. Vectors may be both autonomously replicating and integrative, and the properties of a vector may differ depending on the cellular context (i.e., a vector may be autonomously replicating in one host cell type and purely integrative in another host cell type). Vectors capable of directing the expression of genes to which they are operatively linked are referred to herein as "expression vectors". Vectors that carry an expression construct are generally expression vectors. Vectors have been designed for a variety of cell types. For example, in the bacterium *E. coli*, commonly used vectors include pUC plasmids, pBR322 plasmids, pBlueScript and M13 plasmids. In insect cells (e.g. SF-9, SF-21 and High-Five cells), commonly used vectors include BacPak6 (Clontech) and BaculoGold (Pharmingen) (both Clontech and Pharmingen are divisions of Becton, Dickinson and Co., Franklin Lakes, N.J.). In mammalian cells (e.g. Chinese hamster ovary (CHO) cells, Vaco cells and human embryonic kidney (HEK) cells), commonly used vectors include pCMV vectors (Stratagene, Inc., La Jolla, Calif.), and pRK vectors. In certain embodiments, the application provides cells that comprise a ColoUp2 nucleic acid, particularly a recombinant ColoUp2 nucleic acid, such as an expression construct or vector that comprises a ColoUp2 nucleic acid. Cells may be eukaryotic or prokaryotic, depending on the anticipated use. Prokaryotic cells, especially *E. coli*, are particularly useful for storing and replicating nucleic acids, particularly nucleic acids carried on plasmid or viral vectors. Bacterial cells are also particularly useful for expressing nucleic acids to produce large quantities of recombinant protein, but bacterial cells do not usually mimic eukaryotic post-translational modifications, such as glycosylations or lipid-modifications, and so will tend to be less suitable for production of proteins in which the post-translational modification state is significant. Eukaryotic cells, and especially cell types such as insect cells that work with baculovirus-based protein expression systems, and Chinese hamster ovary cells, are good systems for expressing eukaryotic proteins that have significant post-translational modifications. Eukaryotic cells are also useful for studying various aspects of the function of eukaryotic proteins.

In certain aspects the application further provides methods for preparing ColoUp2 polypeptides. In general, such methods comprise obtaining a cell that comprises a nucleic acid encoding a ColoUp2 polypeptide, and culturing the cell under conditions that cause production of the ColoUp2 polypeptide. Polypeptides produced in this manner may be obtained from the appropriate cell or culture fraction. For example, secreted proteins are most readily obtained from the culture supernatant, soluble intracellular proteins are most readily obtained from the soluble fraction of a cell lysate, and membrane proteins are most readily obtained from a membrane fraction. However, proteins of each type can generally be found in all three types of cell or culture fraction. Crude cellular or culture fractions may be subjected to further purification procedures to obtain substantially purified ColoUp2 polypeptides. Common purification procedures include affinity purification (e.g., with hexahistidine-tagged polypeptides), ion exchange chromatography, reverse phase chromatography, gel filtration chromatography, etc.

In certain aspects, the application provides recombinant, isolated, substantially purified or purified ColoUp2 polypeptides. In certain embodiments, such polypeptides may encode a complete or partial ColoUp2 polypeptide. In certain embodiments, a ColoUp2 polypeptide is composed of natural amino acids, amino acid analogs, or mixtures thereof. ColoUp2 polypeptides may also include one or more post-translational modifications, such as glycosylation, phosphorylation, lipid modification, acetylation, etc. In certain embodiments, the application provides isolated, substantially purified, purified or recombinant polypeptides comprising an amino acid sequence that is at least 90% identical to an amino acid sequence of any of SEQ ID NOs: 1 or 3-4 and optionally at least 95%, 97%, 98%, 99%, 99.3%, 99.5% or 99.7% identical to a nucleic acid of any of SEQ ID NOs: 1 or 3-4. In certain preferred embodiments, the application provides an isolated, substantially purified, purified or recombinant polypeptide comprising an amino acid sequence that differs from SEQ ID NOs: 1 or 3-4 by no more than 4 amino acid substitutions, additions or deletions. Optionally, a polypeptide of the invention comprises an additional moiety, such as an additional polypeptide sequence or other added compound, with a particular function, such as an epitope tag that facilitates detection of the recombinant polypeptide with an antibody, a purification moiety that facilitates purification (e.g., by affinity purification), a detection moiety, that facilitates detection of the polypeptide in vivo or in vitro, or an antigenic moiety that increases the antigenicity of the polypeptide so as to facilitate antibody production. Often, a single moiety will provide multiple functionalities. For example, an epitope tag will generally also assist in purification, because an antibody that recognizes the epitope can be used in an affinity purification procedure as well. Examples of commonly used epitope tags are: an HA tag, a hexahistidine tag, a V5 tag, a Glu-Glu tag, a c-myc tag, a VSV-G tag, a FLAG tag, an enterokinase cleavage site tag and a T7 tag. Commonly used purification moieties include: a hexahistidine tag, a glutathione-S-transferase domain, a cellulose binding domain and a biotin tag. Commonly used detection moieties include fluorescent proteins (e.g., green fluorescent proteins), a biotin tag, and chromogenic/fluorogenic enzymes (e.g., beta-galactosidase and luciferase). Commonly used antigenic moieties include the keyhole limpet hemocyanin and serum albumins. Note that these moieties need not be polypeptides and need not be connected to the polypeptide by a traditional peptide bond.

3. Antibodies and Uses Therefor

Another aspect of the invention pertains to an antibody specifically reactive with a ColoUp2 polypeptide that is effective for decreasing a biological activity of the polypeptides. For example, by using immunogens derived from a ColoUp2 polypeptide, e.g., based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a ColoUp2 polypeptide or an antigenic fragment which is capable of eliciting an antibody response, or a fusion protein). Techniques for conferring immunogenicity on a protein or peptide include conjugation to carriers or other techniques well known in the art. An immunogenic portion of a ColoUp2 polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a ColoUp2 polypeptide of a mammal, e.g., antigenic determinants of a protein set forth in SEQ ID NOs: 1 and 3-4.

In one embodiment, antibodies are specific for the secreted proteins as encoded by nucleic acid sequences as set forth in SEQ ID NO: 2. In another embodiment, the antibodies are immunoreactive with one or more proteins having an amino acid sequence that is at least 80% identical to an amino acid sequence as set forth in SEQ ID NOs: 1 and 3-4. In other embodiments, an antibody is immunoreactive with one or more proteins having an amino acid sequence that is at least 85%, 90%, 95%, 98%, 99%, 99.3%, 99.5%, 99.7% identical or 100% identical to an amino acid sequence as set forth in SEQ ID NOs: 1 or 3-4. In certain preferred embodiments, the invention provides an antibody that binds to an epitope including the C-terminal portion of the polypeptide of SEQ ID NOs: 1 or 3-4. In certain preferred embodiments, the invention provides an antibody that binds to an epitope of a ColoUp2 polypeptide that is prevalent in the blood of an animal having a cancer, such as SEQ ID NO: 1 or 4.

Following immunization of an animal with an antigenic preparation of a ColoUp2 polypeptide, anti-ColoUp2 antisera can be obtained and, if desired, polyclonal anti-ColoUp2 antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a mammalian ColoUp2 polypeptide of the present invention and monoclonal antibodies isolated from a culture comprising such hybridoma cells. In one embodiment antihuman ColoUp2 antibodies specifically react with the protein encoded by a nucleic acid having SEQ ID NO: 2; more preferably the antibodies specifically react with a secreted ColoUp2 protein that is produced by the expression of a nucleic acid having a sequence of SEQ ID NO: 2.

The term "antibody" as used herein is intended to include fragments thereof which are also specifically reactive with one of the subject ColoUp2 polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for a ColoUp2 polypeptide conferred by at least one CDR region of the antibody. In preferred embodiments, the antibodies, the antibody further comprises a label attached thereto and able to be detected, (e.g., the label can be a radioisotope, fluorescent compound, enzyme or enzyme co-factor).

In certain preferred embodiments, an antibody of the invention is a monoclonal antibody, and in certain embodiments the invention makes available methods for generating novel antibodies. For example, a method for generating a monoclonal antibody that binds specifically to a ColoUp2 polypeptide may comprise administering to a mouse an amount of an immunogenic composition comprising the ColoUp2 polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the ColoUp2 polypeptide. Once obtained, a hybridoma can be propagated in a cell culture, optionally in culture conditions where the hybridoma-derived cells produce the monoclonal antibody that binds specifically to the ColoUp2 polypeptide. The monoclonal antibody may be purified from the cell culture.

Anti-ColoUp2 antibodies can be used, e.g., to detect ColoUp2 polypeptides in biological samples and/or to monitor ColoUp2 polypeptide levels in an individual, for determining whether or not said patient is likely to develop a cancer or is more likely to harbor a cancer, or allowing determination of the efficacy of a given treatment regimen for an individual afflicted with cancer. The level of ColoUp2 polypeptide may be measured in a variety of sample types such as, for example, in cells, stools, and/or in bodily fluid, such as in whole blood samples, blood serum, blood plasma and urine. The adjective "specifically reactive with" as used in reference to an antibody is intended to mean, as is generally understood in the art, that the antibody is sufficiently selective between the antigen of interest (e.g., a ColoUp2 polypeptide) and other antigens that are not of interest that the antibody is useful for, at minimum, detecting the presence of the antigen of interest in a particular type of biological sample. In certain methods employing the antibody, a higher degree of specificity in binding may be desirable. For example, an antibody for use in detecting a low abundance protein of interest in the presence of one or more very high abundance protein that are not of interest may perform better if it has a higher degree of selectivity between the antigen of interest and other cross-reactants. Monoclonal antibodies generally have a greater tendency (as compared to polyclonal antibodies) to discriminate effectively between the desired antigens and cross-reacting polypeptides. In addition, an antibody that is effective at selectively identifying an antigen of interest in one type of biological sample (e.g., a stool sample) may not be as effective for selectively identifying the same antigen in a different type of biological sample (e.g., a blood sample). Likewise, an antibody that is effective at identifying an antigen of interest in a purified protein preparation that is devoid of other biological contaminants may not be as effective at identifying an antigen of interest in a crude biological sample, such as a blood or urine sample. Accordingly, in preferred embodiments, the application provides antibodies that have demonstrated specificity for an antigen of interest (e.g., a ColoUp2 polypeptide) in a sample type that is likely to be the sample type of choice for use of the antibody. In a particularly preferred embodiment, the application provides antibodies that bind specifically to a ColoUp2 polypeptide in a protein preparation from blood (optionally serum or plasma) from a patient that has a cancer or that bind specifically in a crude blood sample (optionally a crude serum or plasma sample).

One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g., by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays and immunohistochemistry.

Another application of anti-ColoUp2 antibodies of the present invention is in the immunological screening of cDNA libraries constructed in expression vectors such as gt11, gt18-23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxy termini consist of a foreign polypeptide. Antigenic epitopes of a ColoUp2 polypeptide, e.g., other orthologs of a particular protein or other paralogs from the same species, can then be detected with antibodies, such as, for example, reacting nitrocellulose filters lifted from infected plates with the appropriate anti-ColoUp2 antibodies. Positive phage detected by this assay can then be isolated from the infected plate. Thus, the presence of ColoUp2 homologs can be detected and cloned from other animals, as can alternate isoforms (including splice variants) from humans.

4. Methods for Detecting Molecular Markers in a Patient

In certain embodiments, the invention provides methods for detecting molecular markers, such as proteins or nucleic acid transcripts of the ColoUp2 markers described herein. In certain embodiments, a method of the invention comprises providing a biological sample and probing the biological sample for the presence of a ColoUp2 marker. Information regarding the presence or absence of the ColoUp2 marker, and optionally the quantitative level of the ColoUp2 marker, may then be used to draw inferences about the nature of the biological sample and, if the biological sample was obtained from a subject, the health state of the subject.

Samples for use with the methods described herein may be essentially any biological material of interest. For example, a sample may be a tissue sample from a subject, a fluid sample from a subject, a solid or semi-solid sample from a subject, a primary cell culture or tissue culture of materials derived from a subject, cells from a cell line, or medium or other extracellular material from a cell or tissue culture, or a xenograft (meaning a sample of a cancer from a first subject, such as a human, that has been cultured in a second subject, e.g., an immunocompromised mouse). The term "sample" as used herein is intended to encompass both a biological material obtained directly from a subject (which may be described as the primary sample) as well as any manipulated forms or portions of a primary sample. For example, in certain embodiments, a preferred fluid sample is a blood sample. In this case, the term sample is intended to encompass not only the blood as obtained directly from the patient but also fractions of the blood, such as plasma, serum, cell fractions (e.g., platelets, erythrocytes, lymphocytes), protein preparations, nucleic acid preparations, etc. A sample may also be obtained by contacting a biological material with an exogenous liquid, resulting in the production of a lavage liquid containing some portion of the contacted biological material. Furthermore, the term "sample" is intended to encompass the primary sample after it has been mixed with one or more additive, such as preservatives, chelators, anti-clotting factors, etc. In certain embodiments, a fluid sample is a urine sample. In certain embodiments, a preferred solid or semi-solid sample is a stool sample. In certain embodiments, a preferred tissue sample is a biopsy from a tissue known to harbor or suspected of harboring a neoplasia. In certain embodiments, a preferred cell culture sample is a sample comprising cultured cells of a cancer cell line. A subject is preferably a human subject, but it is expected that the molecular markers disclosed herein, and particularly their homologs from other animals, are of similar utility in other animals. In certain embodiments, it may be possible to detect a marker directly in an organism without obtaining a separate portion of biological material. In such instances, the term sample is intended to encompass that portion of biological material that is contacted with a reagent or device involved in the detection process.

In certain embodiments, a method of the invention comprises detecting the presence of a ColoUp2 protein in a sample. Optionally, the method involves obtaining a quantitative measure of the ColoUp2 protein in the sample. In view of this specification, one of skill in the art will recognize a wide range of techniques that may be employed to detect and optionally quantitate the presence of a protein. In preferred embodiments, a ColoUp2 protein is detected with an antibody. Suitable antibodies are described in a separate section below. In many embodiments, an antibody-based detection assay involves bringing the sample and the antibody into contact so that the antibody has an opportunity to bind to proteins having the corresponding epitope. In many embodiments, an antibody-based detection assay also typically involves a system for detecting the presence of antibody-epitope complexes, thereby achieving a detection of the presence of the proteins having the corresponding epitope. Antibodies may be used in a variety of detection techniques, including enzyme-linked immunosorbent assays (ELISAs), immunoprecipitations, Western blots. Antibody-independent techniques for identifying a protein may also be employed. For example, mass spectroscopy, particularly coupled with liquid chromatography, permits detection and quantification of large numbers of proteins in a sample. Two-dimensional gel electrophoresis may also be used to identify proteins, and may be coupled with mass spectroscopy or other detection techniques, such as N-terminal protein sequencing. RNA aptamers with specific binding for the protein of interest may also be generated and used as a detection reagent.

In certain preferred embodiments, methods of the invention involve detection of a secreted form of a ColoUp2 protein.

Samples should generally be prepared in a manner that is consistent with the detection system to be employed. For example, a sample to be used in a protein detection system should generally be prepared in the absence of proteases. Likewise, a sample to be used in a nucleic acid detection system should generally be prepared in the absence of nucleases. In many instances, a sample for use in an antibody-based detection system will not be subjected to substantial preparatory steps. For example, urine may be used directly, as may saliva and blood, although blood will, in certain preferred embodiments, be separated into fractions such as plasma and serum.

In certain embodiments, a method of the invention comprises detecting the presence of a ColoUp2 expressed nucleic acid, such as an mRNA, in a sample. Optionally, the method involves obtaining a quantitative measure of the ColoUp2 expressed nucleic acid in the sample. In view of this specification, one of skill in the art will recognize a wide range of techniques that may be employed to detect and optionally quantitate the presence of a nucleic acid. Nucleic acid detection systems generally involve preparing a purified nucleic acid fraction of a sample, and subjecting the sample to a direct detection assay or an amplification process followed by a detection assay. Amplification may be achieved, for example, by polymerase chain reaction (PCR), reverse transcriptase (RT) and coupled RT-PCR. Detection of a nucleic acid is generally accomplished by probing the purified nucleic acid fraction with a probe that hybridizes to the nucleic acid of interest, and in many instances detection involves an amplification as well. Northern blots, dot blots, microarrays, quantitative PCR and quantitative RT-PCR are all well known methods for detecting a nucleic acid in a sample.

In certain embodiments, the invention provides nucleic acid probes that bind specifically to a ColoUp2 nucleic acid. Such probes may be labeled with, for example, a fluorescent moiety, a radionuclide, an enzyme or an affinity tag such as a biotin moiety. For example, the TaqMan® system employs nucleic acid probes that are labeled in such a way that the fluorescent signal is quenched when the probe is free in solution and bright when the probe is incorporated into a larger nucleic acid.

In certain embodiments, the application provides methods for imaging tumors or cancerous tissues by targeting antibodies to the ColoUp2 marker. The ColoUp2 marker may be targeted using monoclonal antibodies which may be labeled with radioisotopes for clinical imaging of tumors or with toxic agents to destroy them.

In other embodiments, the application provides methods for administering a imaging agent comprising a targeting moiety and an active moiety. The targeting moiety may be an antibody, Fab, F(Ab)2, a single chain antibody or other binding agent that interacts with an epitope specified by a polypeptide sequence having an amino acid sequence as set forth in SEQ ID NOs: 1 or 3-4. The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. The imaging agent is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography.

Immunoscintigraphy using monoclonal antibodies directed at the ColoUp2 marker may be used to detect and/or diagnose tumors or cancerous tissues. For example, monoclonal antibodies against the ColoUp2 marker labeled with. $^{99}$Technetium, $^{111}$Indium, $^{125}$Iodine—may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

5. Immunogenic ColoUp2 Proteins

In certain embodiments, the invention relates to methods for identifying ColoUp2 proteins that elicit an immune response in subjects. In one aspect, these immunogenic ColoUp2 polypeptides have an amino acid sequence that is at least 90%, 95%, or 98-99% identical to the amino acid sequences as set forth in SEQ ID NOs: 1 or 3-4. In certain embodiments, such proteins may be suitable as components in a vaccine or for the generation of antibodies that may be used to treat cancers.

In certain embodiments, ColoUp2 proteins that elicit a humoral response may be identified as follows. Sera and/or tissue are obtained from a subject that has been treated for a cancer by immunotherapy. Proteins from the cancer tissue sample will be contacted with antibodies (either purified or in crude serum) to identify proteins that react with the antibodies. The sera or tissue may be obtained, for example, from a center involved in cancer immunotherapy.

In one embodiment, ColoUp2 proteins that elicit a humoral response may be identified by contacting proteins isolated from a cancer sample with antibodies obtained from the serum (or simply serum itself or fractions thereof) of a subject having a cancer. Proteins that react with an antibody from the subject having a cancer are likely to be proteins that elicit a humoral response. Optionally, the reactivity of proteins is tested against serum or antibodies from a subject not having a cancer as a comparison, and preferably the antibodies or serum are from the same subject, but at a point in time when the subject did not have a cancer.

For these methods, proteins may be analyzed in any of the various methods described herein or by other methods that, in view of this specification, are considered to be appropriate by one of skill in the art.

As discussed above, exemplary ColoUp2 polypeptides include SEQ ID NOs: 1 and 3-4. ColoUp2 polypeptides are further understood to include variants, such as variants of SEQ ID NOs: 1 and 3-4.

In another aspect, the invention provides polypeptides that are agonists or antagonists of a ColoUp2 polypeptide. Variants and fragments of a ColoUp2 polypeptide may have a hyperactive or constitutive activity, or, alternatively, act to prevent a ColoUp2 polypeptide from performing one or more functions. For example, a truncated form lacking one or more domain may have a dominant negative effect.

It is also possible to modify the structure of the subject ColoUp2 polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the ColoUp2 polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W. H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of a ColoUp2 polypeptide can be assessed, e.g., for their ability to bind to another polypeptide, e.g., another ColoUp2 polypeptide. Polypeptides in which more than one replacement has taken place can readily be tested in the same manner.

This invention further contemplates a method of generating sets of combinatorial mutants of the subject ColoUp2 polypeptides, as well as truncation mutants, and is especially useful for identifying potential variant sequences (e.g., homologs). The purpose of screening such combinatorial libraries is to generate, for example, ColoUp2 homologs which can act as either agonists or antagonist, or alternatively, which possess novel activities all together. Combinatorially-derived homologs can be generated which have a selective potency relative to a naturally occurring ColoUp2 polypeptide. Such proteins, when expressed from recombinant DNA constructs, can be used in gene therapy protocols.

Likewise, mutagenesis can give rise to homologs which have intracellular half-lives dramatically different than the corresponding wild-type protein. For example, the altered protein can be rendered either more stable or less stable to proteolytic degradation or other cellular process which result in destruction of, or otherwise inactivation of the ColoUp2 polypeptide of interest. Such homologs, and the genes which encode them, can be utilized to alter the levels of a ColoUp2 protein of interest by modulating the half-life of the protein. For instance, a short half-life can give rise to more transient biological effects and, when part of an inducible expression system, can allow tighter control of recombinant ColoUp2 polypeptide levels within the cell. As above, such proteins, and particularly their recombinant nucleic acid constructs, can be used in gene therapy protocols.

In similar fashion, homologs of a ColoUp2 polypeptide can be generated by the present combinatorial approach to act as antagonists, in that they are able to interfere with the ability of the corresponding wild-type protein to function.

Alternatively, other forms of mutagenesis can be utilized to generate a combinatorial library. For example, a ColoUp2 protein homolog (both agonist and antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137: 109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193: 653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of a ColoUp2 polypeptide.

The invention also provides for reduction of the subject ColoUp2 polypeptides to generate mimetics, e.g., peptide or non-peptide agents, which are able to mimic the behavior or biological activity of the authentic protein. Such mutagenic techniques as described above, as well as the thioredoxin system, are also particularly useful for mapping the determinants of a ColoUp2 polypeptide which participate in protein-protein interactions involved in, for example, cancers.

6. ColoUp2 Nucleic Acids

In certain aspects, the invention provides nucleic acids that encode ColoUp2 proteins. In one aspect, the nucleic acid sequences are at least 90%, 95%, or 98-99% identical to the nucleic acid sequences as set forth in SEQ ID NO: 2. In some embodiments, such nucleic acids include nucleic acids that are differentially expressed in cancer samples versus a control sample. In further embodiments, ColoUp2 nucleic acids encode proteins that are differentially present or absent (or at a different level or in altered form) in the blood of a subject having a cancer versus a subject not having a cancer. In yet additional embodiments, ColoUp2 nucleic acids include nucleic acids encoding proteins that are differentially expressed (including altered forms etc.) in cancer samples versus a control sample. ColoUp2 nucleic acids are further understood to include nucleic acids that encode variants, such as variants of SEQ ID NO: 2 and nucleic acids encoding SEQ ID NOs: 1 or 3-4. Variant nucleotide sequences include sequences that differ by one or more nucleotide substitutions, additions or deletions, such as allelic variants; and will, therefore, include coding sequences that differ from the nucleotide sequence of the coding sequence due to the degeneracy of the genetic code. In other embodiments, variants will also include sequences that will hybridize under highly stringent conditions to a nucleotide sequence of SEQ ID NO: 2 or nucleic acids encoding SEQ ID NOs: 1 or 3-4.

One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

ColoUp2 nucleic acids include nucleic acids which differ from an identified sequence due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. This is particularly likely in the case of nucleic acids derived from cancer samples and proteins that elicit a humoral response in subjects having a cancer. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, oligonucleotides of the invention may be used as diagnostic reagents to detect the presence or absence of the target DNA or RNA sequences to which they specifically bind, such as for determining the level of expression of a gene of the invention or for determining whether a gene of the invention contains a genetic lesion.

7. RNA Interference, Ribozymes, Antisense and DNA Enzyme

In certain aspects, the invention relates to RNAi, ribozyme, antisense and other nucleic acid-related methods and compositions for manipulating (typically decreasing) ColoUp2 expression or activity.

Certain embodiments of the invention make use of materials and methods for effecting knockdown of ColoUp2 gene by means of RNA interference (RNAi). RNAi is a process of sequence-specific post-transcriptional gene repression which can occur in eukaryotic cells. In general, this process involves degradation of an mRNA of a particular sequence induced by double-stranded RNA (dsRNA) that is homologous to that sequence. Any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, RNAi may be effected by introduction or expression of relatively short homologous dsRNAs.

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides of the invention may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al. (2001) Nature 411: 494-8). Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable the skilled artisan. Exemplary dsRNAs may be synthesized chemically or produced in vitro or in vivo using appropriate expression vectors. Exemplary synthetic RNAs include 21 nucleotide RNAs chemically synthesized using methods known in the art (e.g. Expedite RNA phophoramidites and thymidine phosphoramidite (Proligo, Germany). Synthetic oligonucleotides are preferably deprotected and gel-purified using methods known in the art (see e.g. Elbashir et al. (2001) Genes Dev. 15: 188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a ColoUp2 nucleic acid, such as, for example, a nucleic acid that hybridizes, under stringent and/or physiological conditions, to SEQ ID NO: 2 and a complement thereof.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference. Messenger RNA (mRNA) is generally thought of as a linear molecule which contains the information for directing protein synthesis within the sequence of ribonucleotides, however studies have revealed a number of secondary and tertiary structures that exist in most mRNAs. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al. (1989) Proc. Natl. Acad. Sci. USA 86:7706 (1989); and Turner et al. (1988) Annu. Rev. Biophys. Biophys. Chem. 17:167). The rules are useful in identification of RNA structural elements and, in particular, for identifying single stranded RNA regions which may represent preferred segments of the mRNA to target for silencing RNAi, ribozyme or antisense technologies. Accordingly, preferred segments of the mRNA target can be identified for design of the RNAi mediating dsRNA oligonucleotides as well as for design of appropriate ribozyme and hammerhead ribozyme compositions of the invention.

The dsRNA oligonucleotides may be introduced into the cell by transfection with an heterologous target gene using carrier compositions such as liposomes, which are known in the art—e.g. Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al. (1998) J Cell Biol 141: 863-74). The effectiveness of the RNAi may be assessed by any of a number of assays following introduction of the dsRNAs. These include Western blot analysis using antibodies which recognize the ColoUp2 gene product following sufficient time for turnover of the endogenous pool after new protein synthesis is repressed, reverse transcriptase polymerase chain reaction and Northern blot analysis to determine the level of existing ColoUp2 target mRNA.

Further compositions, methods and applications of RNAi technology are provided in U.S. Pat. Nos. 6,278,039, 5,723, 750 and 5,244,805, which are incorporated herein by reference.

Ribozyme molecules designed to catalytically cleave ColoUp2 mRNA transcripts can also be used to prevent translation of subject ColoUp2 mRNAs and/or expression of ColoUp2 (see, e.g., PCT International Publication WO90/11364, published Oct. 4, 1990; Sarver et al. (1990) Science 247:1222-1225 and U.S. Pat. No. 5,093,246). Ribozymes are enzymatic RNA molecules capable of catalyzing the specific cleavage of RNA. (For a review, see Rossi (1994) Current Biology 4: 469-471). The mechanism of ribozyme action involves sequence specific hybridization of the ribozyme molecule to complementary target RNA, followed by an endonucleolytic cleavage event. The composition of ribozyme molecules preferably includes one or more sequences complementary to a ColoUp2 mRNA, and the well known catalytic sequence responsible for mRNA cleavage or a functionally equivalent sequence (see, e.g., U.S. Pat. No. 5,093,246, which is incorporated herein by reference in its entirety).

While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach ((1988) Nature 334:585-591; and see PCT Appln. No. WO89/05852, the contents of which are incorporated herein by reference). Hammerhead ribozyme sequences can be embedded in a stable RNA such as a transfer RNA (tRNA) to increase cleavage efficiency in vivo (Perriman et al. (1995) Proc. Natl. Acad. Sci. USA, 92: 6175-79; de Feyter, and Gaudron, Methods in Molecular Biology, Vol. 74, Chapter 43, "Expressing Ribozymes in Plants", Edited by Turner, P. C, Humana Press Inc., Totowa, N.J.). In particular, RNA polymerase HI-mediated expression of tRNA fusion ribozymes are well known in the art (see Kawasaki et al. (1998) Nature 393: 284-9; Kuwabara et al. (1998) Nature Biotechnol. 16: 961-5; and Kuwabara et al. (1998) Mol. Cell 2: 617-27; Koseki et al. (1999) J Virol 73: 1868-77; Kuwabara et al. (1999) Proc Natl Acad Sci USA 96: 1886-91; Tanabe et al. (2000) Nature 406: 473-4). There are typically a number of potential hammerhead ribozyme cleavage sites within a given target cDNA sequence. Preferably the ribozyme is engineered so that the cleavage recognition site is located near the 5' end of the target mRNA—to increase efficiency and minimize the intracellular accumulation of non-functional mRNA transcripts. Furthermore, the use of any cleavage recognition site located in the target sequence encoding different portions of the C-terminal amino acid domains of, for example, long and short forms of target would allow the selective targeting of one or the other form of the target, and thus, have a selective effect on one form of the target gene product.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a ColoUp2 mRNA, such as an mRNA of a sequence represented in SEQ ID NO: 2. In addition, ribozymes possess highly specific endoribonuclease activity, which autocatalytically cleaves the target sense mRNA. The present invention extends to ribozymes which hybridize to a sense mRNA encoding a ColoUp2 gene such as a therapeutic drug target candidate gene, thereby hybridising to the sense mRNA and cleaving it, such that it is no longer capable of being translated to synthesize a functional polypeptide product.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation. Because ribozymes, unlike antisense molecules, are catalytic, a lower intracellular concentration is required for efficiency.

A further aspect of the invention relates to the use of the isolated "antisense" nucleic acids to inhibit expression, e.g., by inhibiting transcription and/or translation of a subject ColoUp2 nucleic acid. The antisense nucleic acids may bind to the potential drug target by conventional base pair complementarity, or, for example, in the case of binding to DNA duplexes, through specific interactions in the major groove of the double helix. In general, these methods refer to the range of techniques generally employed in the art, and include any methods that rely on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a ColoUp2 polypeptide. Alternatively, the antisense construct is an oligonucleotide probe, which is generated ex vivo and which, when introduced into the cell causes inhibition of expression by hybridizing with the mRNA and/or genomic sequences of a ColoUp2 nucleic acid. Such oligonucleotide probes are preferably modified oligonucleotides, which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

With respect to antisense DNA, oligodeoxyribonucleotides derived from the translation initiation site, e.g., between the −10 and +10 regions of the ColoUp2 gene, are preferred. Antisense approaches involve the design of oligonucleotides (either DNA or RNA) that are complementary to mRNA encoding the ColoUp2 polypeptide. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a gene could be used in an antisense approach to inhibit translation of that mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5',3' or coding region of mRNA, antisense nucleic acids should be at least six nucleotides in length, and are preferably less that about 100 and more preferably less than about 50, 25, 17 or 10 nucleotides in length.

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose. The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

A further aspect of the invention relates to the use of DNA enzymes to inhibit expression of ColoUp2 gene. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid.

There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo include methods of delivery RNA ribozyme, as outlined in detail above. Additionally, one of skill in the art will recognize that, like antisense oligonucleotide, DNA enzymes can be optionally modified to improve stability and improve resistance to degradation.

Antisense RNA and DNA, ribozyme, RNAi constructs of the invention may be prepared by any method known in the art for the synthesis of DNA and RNA molecules, including techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

8. Cancer Therapeutics

In certain aspects, the present invention provides methods of treating cancers and methods of identifying therapeutics for treatment of cancers. As described herein, the term "cancer" includes a tumor inside an individual, a tumor xenograft, or a tumor cultured in vitro. Exemplary forms of cancers (tumors) include, but are not limited to, prostate cancer, bladder cancer, lung cancer (including either small cell or non-small cell cancer), kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer include cancers comprising ColoUp2-expressing cells. In certain embodiments, the tumor is a metastatic tumor.

Specific exemplary forms of cancers include, but are not limited to, endometrial cancer, renal cancer, adenocarcinoma of the lung, stomach cancer, pancreas cancer, breast cancer, prostate cancer or ovarian cancer.

In certain embodiments, the subject cancer therapeutics may inhibit the expression of a ColoUp2 protein. Such inhibitory effects can be at the transcriptional level, at the translational level, or at the post-translational level. In certain embodiments, such therapeutics may affect the function of a ColoUp2 polypeptide such as one selected from the group consisting of SEQ ID NOs: 1 and 3-4. In other embodiments, such therapeutics may be targeted to a cancer by binding to a ColoUp2 protein with or without affecting the activity of the ColoUp2 protein. For example, an aptamer that binds to a ColoUp2 protein may be conjugated to an anti-cancer therapeutic so as to target the therapeutic to cancer cells. In certain embodiments, the anti-ColoUp2 antibodies as described above may be used in the therapy of cancers. Such anti-ColoUp2 antibodies may be conjugated with radio-nucleotides or cytotoxic agents. Anti-ColoUp2 antibodies for cancer therapy may also include antibodies against cell surface exposed epitopes of a ColoUp2 protein.

Optionally, the method further includes additional anti-neoplastic chemotherapeutic compounds that inhibit tumor cells in an additive or synergistic manner with the disclosed ColoUp2-targeted therapeutics. A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

In certain embodiments, candidate therapeutics may be identified on the basis of their ability to modulate the expression of a ColoUp2 protein. To illustrate, the assay may detect agents which modulate the promoter activity of a ColoUp2 gene. In certain embodiments, candidate therapeutics may be identified on the basis of their ability to modulate the binding of a ColoUp2 polypeptide to an associated protein or ligand. In a further embodiment, the assay detects agents which modulate the intrinsic biological activity of a ColoUp2 polypeptide.

A variety of assay formats will suffice and, in light of the present disclosure, those not expressly described herein will nevertheless be comprehended by one of ordinary skill in the art. Assay formats which approximate such conditions as formation of protein complexes, ligand binding, protein activity, or promoter activity can be generated in many different forms, and include assays based on cell-free systems, e.g., purified proteins or cell lysates, as well as cell-based assays which utilize intact cells. Agents to be tested may be generated in essentially any way, such as, for example, by production in bacteria, yeast or other organisms (e.g., natural products), produced chemically (e.g., small molecules, including peptidomimetics), or produced recombinantly. In a preferred embodiment, the test agent is a small organic molecule, e.g., other than a peptide or oligonucleotide, having a molecular weight of less than about 2,000 daltons.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In an exemplary binding assay, the compound of interest is contacted with a mixture comprising a ColoUp2 polypeptide and at least one interacting polypeptide or ligand. Detection and quantification of bound ColoUp2 polypeptide complexes provides a means for determining the compound's efficacy at inhibiting or potentiating interaction. The efficacy of the compound can be assessed by generating dose response curves from data obtained using various concentrations of the test compound. Moreover, a control assay can also be performed to provide a baseline for comparison. In the control assay, the binding is quantitated in the absence of the test compound. Complex formation between a ColoUp2 polypeptide and an interactor may be detected by a variety of techniques, many of which are effectively described above. For instance, modulation in the formation of complexes can be quantitated using, for example, detectably labeled proteins (e.g., radiolabeled, fluorescently labeled, or enzymatically labeled), by immunoassay, or by chromatographic detection. Surface plasmon resonance systems, such as those available from BiaCore, Inc., may also be used to detect protein-protein interaction.

Often, it will be desirable to immobilize one of the polypeptides to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST-fusion proteins can be adsorbed onto glutathione sepharose beads (Sigma Chemical, St. Louis, Mo.) or glutathione derivatized microtitre plates, which are then combined with a potential interacting protein, e.g., an $^{35}$S-labeled polypeptide, and the test compound and incubated under conditions conducive to complex formation.

The ColoUp2 marker and/or profile may be used to screen for therapeutics for a disease state such as cancers. Cell surface proteins associated with a disease state may be diminished or eliminated by treatment with certain test compounds. Such test compounds may be useful as therapeutics for the disease state. In addition, certain test compounds may increase the presence of cell surface proteins that are normally present on healthy cells but diminished or absent in diseased cells. Such test compounds may also be useful as therapeutics of cancers. Particularly preferred therapeutics will cause the cell surface protein profile of a diseased cell to more closely resemble the cell surface protein profile of a healthy cell.

In further embodiments, the differences between healthy and cancer tissue samples may be analyzed to identify targets for therapeutic screening, and a screen may be designed to identify compounds that bind or otherwise affect the activity of the given target. For example, over-expression of ColoUp2 is detected in various cancer types, such as cancers of endometrium, kidney, lung, stomach, pancreas, breast, prostate, ovary, uterus, and thyroid. Therapeutics that diminish this over-expression may be useful as cancer therapeutics.

In certain embodiments, a method for selecting an appropriate cancer therapeutic for a subject is a computer-assisted method. Such a method may comprise obtaining a cell surface protein profile or measuring a marker protein in a sample from a subject. The output signal may then be compared against a database comprising output signal information from a plurality of subjects and further comprising clinical status information from a plurality of subjects. It is contemplated that one may use a computer interface to identify in the database any clinical conditions correlated with the protein profile or marker. Accordingly, one may select a targeted therapeutic to ameliorate or prevent the correlated condition.

9. Tumor Vaccines

The treatment of cancer with tumor vaccines has been a goal of physicians and scientists ever since effective immunization against infectious disease with vaccines was developed. In the past, major tumor antigens had not been molecularly characterized. Recent advances are, however, beginning to define potential molecular targets and strategies and this had evolved with the principle that T-cell mediated responses are a useful target for approaches to cancer immunization. In addition, these antigens are not truly foreign and tumor antigens fit more with a self/altered self paradigm, compared to a non-self paradigm for antigens recognized in infectious diseases. Antigens that have been used in the art include the glycolipids and glycoproteins e.g., gangliosides, the developmental antigens, e.g., MAGE, tyrosinase, melan-A and gp75, and mutant oncogene products, e.g., p53, ras, and HER-2/neu. Vaccine possibilities include purified proteins and glycolipids, peptides, cDNA expressed in various vectors, and a range of immune adjuvants. Any ColoUp2 protein may be selected for use in a tumor vaccine, although as noted above, ColoUp2 proteins that elicit a humoral response in subjects having a cancer are preferred.

Yet another aspect of the present invention relates to the modification of tumor cells, and/or the immune response to tumor cells in a patient by administering a vaccine to enhance the anti-tumor immune response in a host. The present invention provides, for examples, tumor vaccines based on administration of expression vectors encoding a ColoUp2 gene, or portions thereof, or immunogenic preparations of polypeptides.

In general, it is noted that malignant transformation of cells is commonly associated with phenotypic changes. Such changes can include loss, gain, or alteration in the level of expression of certain proteins. It has been observed that in some situations the immune system may be capable of recognizing a tumor as foreign and, as such, mounting an immune response against the tumor (Kripke, M., Adv. Cancer Res. 34, 69-75 (1981)). This hypothesis is based in part on the existence of phenotypic differences between tumor cells and normal cells, which is supported by the identification of tumor associated antigens (TAAs) (Schreiber, H., et al. Ann. Rev. Immunol. 6, 465-483 (1988)). TAAs are thought to distinguish a transformed cell from its normal counterpart. For example, three genes encoding TAAs expressed in melanoma cells, MAGE-1, MAGE-2 and MAGE-3, have been cloned (van der Bruggen, P., et al. Science 254, 1643-1647 (1991)). That tumor cells under certain circumstances can be recognized as foreign is also supported by the existence of T cells which can recognize and respond to tumor associated antigens presented by MHC molecules. Such TAA-specific T lymphocytes have been demonstrated to be present in the immune repertoire and are capable of recognizing and stimulating an immune response against tumor cells when properly stimulated in vitro (Rosenberg, S. A., et al. Science 233, 1318-1321 (1986); Rosenberg, S. A. and Lotze, M. T. Ann. Rev. Immunol. 4, 681-709 (1986)). In the case of melanoma cells both the tyrosinase gene (Brichard, V., et al. J. Exp. Med. 178:489 (1993)) and the Melan-A gene (Coulie et al. J. Exp. Med. 180:35)) have been identified as genes coding for antigens recognized on melanoma cells by autologous cytotoxic lymphocytes.

Induction of T lymphocytes is often a significant early step in a host's immune response. Activation of T cells results in cytokine production, T cell proliferation, and generation of T cell-mediated effector functions. T cell activation requires an antigen-specific signal, often called a primary activation signal, which results from stimulation of a clonally-distributed T cell receptor (TcR) present on the surface of the T cell. This antigen-specific signal is usually in the form of an antigenic peptide bound either to a major histocompatibility complex (MHC) class I protein or an MHC class II protein present on the surface of an antigen presenting cell (APC). CD4+, helper T cells recognize peptides associated with class II molecules which are found on a limited number of cell types, primarily B cells, monocytes/macrophages and dendritic cells. In most cases class II molecules present peptides derived from proteins taken up from the extracellular environment. In contrast, CD8+, cytotoxic T cells (CTL) recognize peptides associated with class I molecules. Class I molecules are found on almost all cell types and, in most cases, present peptides derived from endogenously synthesized proteins.

The importance of T cells in tumor immunity has several implications which are important in the development of anti-tumor vaccines. Since antigens are processed and presented before they are recognized by T cells, they may be derived from any protein of the tumor cell, whether extracellular or intracellular. In addition, the primary amino acid sequence of the antigen is more important than the three-dimensional structure of the antigen. Tumor vaccine strategies may use the tumor cell itself as a source of antigen, or may be designed to enhance responses against specific gene products. (Pardoll, D. 1993. Annals of the New York Academy of Sciences 690: 301).

The present invention provides for various tumor vaccination methods and reagents which can be used to elicit an anti-tumor response against transformed cells which express/display a ColoUp2 polypeptide, or which have been engineered to present an antigen of a ColoUp2 polypeptide. In general, the tumor vaccine strategies of the present invention fall into two categories: (1) strategies that use the tumor cell itself as a source of tumor antigen, and (2) antigen-specific vaccine strategies that are designed to generate immune responses against specific antigens of a ColoUp2 polypeptide.

In general, a ColoUp2 vaccine polypeptide will include at least a portion of the ColoUp2 polypeptide, optionally including a site of mutation which, when occurring in the full-length protein, results in loss of its biological activity. Where the cancer vaccine comprises a sufficient portion of a ColoUp2 protein, the protein can be further mutated to render the vaccine polypeptide biologically inactive.

In one embodiment, a tumor cell which otherwise does not express a mutant ColoUp2 polypeptide can be rendered immunogenic as a target for CTL recognition by association of a ColoUp2 vaccine polypeptide. For example, this can be accomplished by the use of gene transfer vectors. Such gene transfer vectors may be administered in any biologically effective carrier, e.g., any formulation or composition capable of effectively delivering the ColoUp2 vaccine gene to cells in vivo. Alternatively, cells from the patient or other host organism can be transfected with the tumor vaccine construct ex vivo, allowed to express the ColoUp2 protein, and, preferably after inactivation by radiation or the like, administered to an individual. In particular, viral vectors represent an attractive method for delivery of tumor vaccine antigens because viral proteins are expressed de novo in infected cells, are degraded within the cytosol, and are transported to the endoplasmic reticulum where the degraded peptide products associate with MHC class I molecules before display on the cell surface (Spooner et al. (1995) Gene Therapy 2:173).

Approaches include insertion of the subject gene into viral vectors including recombinant retroviruses, adenovirus, adeno-associated virus, vaccinia virus, and herpes simplex virus-1, or plasmids. Viral vectors transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or CaPO4 precipitation carried out in vivo. It will be appreciated that because transduction of appropriate target cells represents the critical first step in gene transfer, choice of the particular gene delivery system will depend on such factors as the phenotype of the intended target and the route of administration, e.g. locally or systemically.

In addition to viral transfer methods, such as those illustrated above, non-viral methods can also be employed to cause expression of a subject ColoUp2 polypeptide in the tissue of an animal in order to elicit a cellular immune response. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the vaccine gene by the targeted cell. Exemplary gene delivery systems of this type include liposomal derived systems, polylysine conjugates, and artificial viral envelopes.

In another embodiment a mutant ColoUp2 peptide of the present invention may be directly delivered to the patient. Although such expression constructs as exemplified above have been shown to be an efficient means by which to obtain expression of peptides in the context of class I molecules, vaccination with isolated peptides has also been shown to result in class I expression of the peptides in some cases. For example, the use of synthetic peptide fragments containing CTL epitopes which are presented by class I molecules has been shown to be an effective vaccine against infection with lymphocytic choriomeningitis virus (Schultz et al. 1991. Proc. Natl. Acad. Sci. USA 88:2283) or sendai virus (Kast et al. 1991. Proc Natl Acad Sci. 88:2283). Subcutaneous administration of a CTL epitope has also been found to render mice resistant to challenge with human papillomavirus 16-transformed tumor cells (Feltkamp et al. (1993) Eur. J. Immunol. 23:2242-2249). It is contemplated that such peptides may be presented in the context of tumor cell class I antigens or by other, host-derived class I bearing cells (Huang et al. 1994. Science 264:961).

The ColoUp2 proteins, and portions thereof, may be used in the preparation of vaccines prepared by known techniques (c.f., U.S. Pat. Nos. 4,565,697; 4,528,217 and 4,575,495). Such polypeptides displaying antigenic regions capable of eliciting protective immune response are selected and incorporated in an appropriate carrier. Alternatively, an antitumor antigenic portion of a ColoUp2 protein may be incorporated into a larger protein by expression of fused proteins.

In other embodiments, the carcinoma cell itself can be used as the source of antitumor ColoUp2 antigens. See, for review, Pardoll, D. 1993. Annals of the New York Academy of Sciences 690:301. For example, cells which have been identified through phenotyping as expressing a mutant ColoUp2 protein can be used to generate a CTL response against a tumor. For example, tumor-infiltrating lymphocytes (TILs) may be derived from tumor biopsies which have such a phenotype. Following such protocols as described by Horn et al. (1991) J Immunotherap 10:153, TILs can be isolated from tumor specimens and grown in the presence of interleukin-2 in order to generate oligoclonal populations of activated T-lymphocytes that are cytolytic to the tumor cells expressing the mutant ColoUp2 protein.

In other embodiments, whole cell vaccines can be used to treat cancer patients. Such vaccines can include, for example, irradiated autologous or allogenic tumor cells which express (endogenously or recombinantly) a mutant ColoUp2 polypeptide (or fragment thereof), or lysates of such cells.

10. Pharmaceutical Compositions and Methods of Administration

In certain aspects, any of the ColoUp2 therapeutic agents of the present invention (e.g., antibodies, peptides, polypeptides, small molecules, RNAi constructs, antisense probes, and tumor vaccines) may be formulated with a pharmaceutically acceptable carrier. Such therapeutic agents can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject therapeutic agents include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

The therapeutic agents may be administered in any conventional manner, including oranasally, subcutaneously, intraperitoneally or intramuscularly. The vaccine may further comprise, as discussed infra, an adjuvant in order to increase the immunogenicity of the vaccine preparation. In some cases, it may be advantageous to couple one or more of the ColoUp2 therapeutic agents to a carrier, in particular a macromolecular carrier. The carrier can be a polymer to which the ColoUp2 therapeutic agent is bound by hydrophobic non-covalent interaction, such as a plastic, e.g., polystyrene, or a polymer to which the agent is covalently bound, such as a polysaccharide, or a polypeptide, e.g., bovine serum albumin, ovalbumin or keyhole limpet hemocyanin. The carrier should preferably be non-toxic and non-allergenic.

In addition, the formulations may also contain one or more stabilizer, exemplary being carbohydrates such as sorbitol, mannitol, starch, sucrose, dextrin, and glucose, proteins such as albumin or casein, and buffers such as alkaline metal phosphate and the like.

In clinical settings, the ColoUp2 therapeutic agent of the present invention can be introduced into a patient by any of a number of methods, each of which is familiar in the art. For instance, a pharmaceutical preparation of the gene delivery system or peptide can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences. In other embodiments, initial delivery of the recombinant gene is more limited with introduction into the animal being quite localized.

Suitable pharmaceutical vehicles for administration to a patient are known to those skilled in the art. For parenteral administration, the ColoUp2 therapeutic agents will usually be dissolved or suspended in sterile water or saline. For enteral administration, the ColoUp2 therapeutic agent can be incorporated into an inert carrier in tablet, liquid, or capsular form. The preparation may also be emulsified or the active ingredient encapsulated in liposome vehicles.

In addition to inhibiting growth of a tumor at its original site, the ColoUp2 therapeutic agents of the current invention may also be used in a method for preventing or treating metastatic spread of a tumor or preventing or treating recurrence of a tumor.

Toxicity and therapeutic efficacy of the ColoUp2 therapeutic compounds (agents) can be determined by standard pharmaceutical procedures in cell cultures or experimental animals, e.g., for determining The Ld50 (The Dose Lethal To 50% Of The Population) And The Ed50 (the dose therapeutically effective in 50% of the population). The dose ratio between toxic and therapeutic effects is the therapeutic index and it can be expressed as the ratio LD50/ED50. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The invention now being generally described, it will be more readily understood by reference to the following examples, which are included merely for purposes of illustration of certain aspects and embodiments of the present invention, and are not intended to limit the invention.

EXEMPLIFICATION

The invention now being generally described, it will be more readily understood by reference to the following examples, which are included merely for purposes of illustration of certain aspects and embodiments of the present invention, and are not intended to limit the invention.

Example 1

ColoUp2 is a Secreted Protein

The ColoUp2 transcript was inserted into a cDNA expression vector with a C-terminal V5 epitope tag. FIG. 4 shows a summary of the behavior of the tagged protein expressed by transfection of the vector into SW480 and Vaco400 cells. An anti V5 western blot shows (red arrows) expression of the transfected tagged protein detected in the lysate of a pellet of transfected cells (lysates western panel, lanes labeled ColoUp2/V5) which is absent in cells transfected with a control empty expression vector (lanes labeled pcDNA3.1). Moreover, serial immunoprecipitation and western blotting of V5 tagged protein from media in which V400 and SW480 cells were growing (which had been clarified by centrifugation prior to immunoprecipitation) also clearly demonstrates secretion of the ColoUp2 protein into the growth medium (panel labeled medium IP-western). Antibody bands from the immunoprecipitation are also present on the IP-western blot. Detection of secreted ColoUp2 protein was shown in cells assayed both 24 hours and 48 hours after transfection.

Cell lines derived from other cancer tissues (e.g., endometrium, kidney, lung, stomach, pancreas, breast, prostate, ovary, uterus, and thyroid) can be similarly analyzed to confirm that ColoUp2 is a secreted protein is these cancer types.

Example 2

ColoUp2 Proteins are Detected in the Blood of Mice

Figure 5:
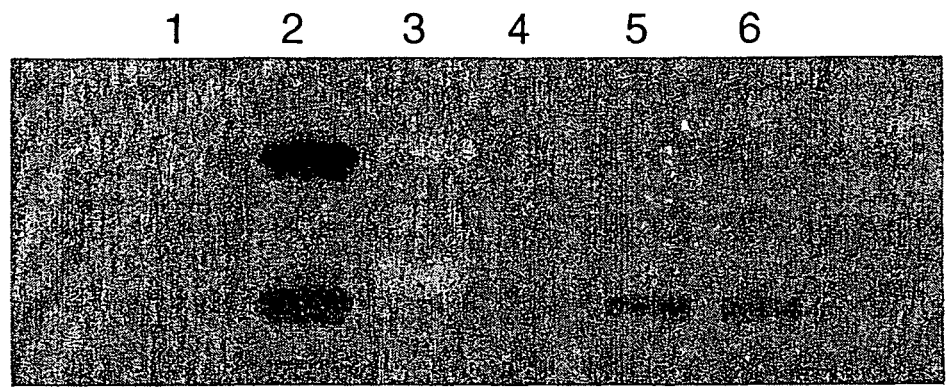
FIG. 5 shows a western blot of V5 tagged ColoUp2 protein detected by anti-V5 antibody. Lane 1: media supernate from SW480 colon cancer cells transfected with an empty expression vector. Lane 2: media supernate from ColoUp2-V5 expressing cells. Lane 3: size markers. Lane 4 shows assay of serum from a mouse xenografted with control SW480 cells corresponding to lane 1. Lanes 5 and 6 show detection of circulating ColoUp2 proteins in blood from two mice bearing human colon cancer xenografts from ColoUp2-V5 expressing SW480 colon cells shown in lane 2. ColoUp2 is secreted as an 85 KD and a companion 55 KD size protein.

To determine that ColoUp2 proteins are effective serologic markers of cancers, we derived transfected cell lines that stably expressed and secreted V5-epitope tagged ColoUp2 proteins. These cells lines were then injected into athymic mice and grown as tumor xenografts. Mice were sacrificed and serum was obtained. V5-tagged proteins were then precipitated from the serum using beads conjugated to anti-V5 antibodies. Precipitated serum proteins were run out on SDS-PAGE, and visualized by western blotting using HRP-conjugated anti-V5 antibodies (thereby eliminating visualization of any contaminating mouse immunoglobulin). FIG. 5 shows detection of circulating ColoUp2 protein in mouse serum. The ColoUp2 protein is secreted as 2 bands of 85 KD and 55 KD in size, of which the 55 KD band predominates in the serum. The 55 KD band is presumably a processed form of the 85 KD band. This observation demonstrates that, in this mouse model, ColoUp2 is indeed a secreted marker of cancers, and that ColoUp2 can gain access to and circulate stably in patient serum. This observation provides the surprising result that a processed fragment of ColoUp2 is the predominant serum form of the protein and therefore detection reagents targeted to this portion would be particularly suitable for diagnostic testing. A time course experiment showed that ColoUp2 protein was detectable in mouse blood at the earliest time assayed, 1 week after injection of ColoUp2 secreting colon cancer cells, at which time xenograft tumor volume as only 100 mm$^3$.

Cell lines derived from other cancer tissues (e.g., endometrium, kidney, lung, stomach, pancreas, breast, prostate, ovary, uterus, and thyroid) can be similarly analyzed in mice to confirm that ColoUp2 proteins can be detected in the blood of mice.

Example 3

Purification of ColoUp2 Proteins

Figure 6:
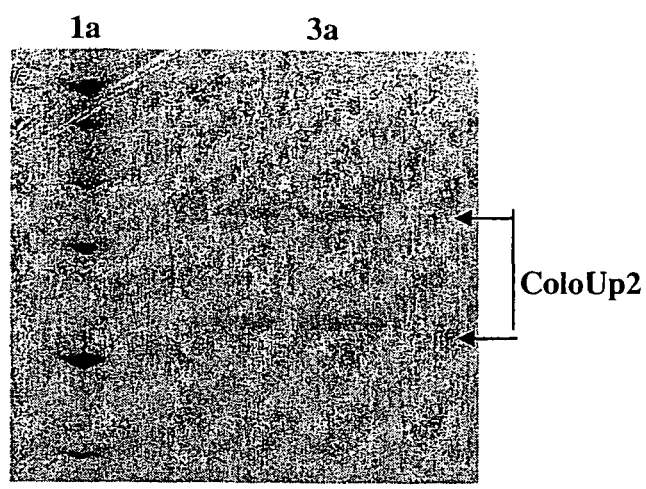

In order to develop monoclonal antibodies against native ColoUp2 proteins, we devised a protocol for purification on Ni-NTA agarose (QIAGEN) nickel beads of recombinant His-tagged ColoUp2 proteins from the media supernate of SW480 cells engineered to express these proteins. Currently we have purified ColoUp2 proteins to sufficient purity to generate antibodies. As shown in FIG. 6, a Coomassie blue stained gel of purified ColoUp2 shows only the 85 KD and 55 KD size bands that correspond to the tagged ColoUp2 proteins visualized on western blot. Thus we have purified ColoUp2 to sufficient homogeneity and yield. Scaled up purification of the proteins from a 50 liter media preparation should yield 2.5 mg of protein, more than adequate for immunizing mice and screening fusion supernates for development of monoclonal antibodies specific for native ColoUp2.

Example 4

Determining the Sequence of the ColoUp2 Fragment

The protein sequence of C-terminal fragment of ColoUp2 that is secreted by human cell lines and detected as predominant fragment in blood (488 aa) was determined. As described above, we have found on western blots and on purified preparations of C-terminal epitope tagged (V5-His epitope) ColoUp2 protein secreted by transfected human colon cancer cells, both a full sized band of approximately 90 kDa and a smaller approximately 55 kDa C-terminal fragment (as demonstrated by the retention of the C-terminal epitope tag). Moreover, when these cells were injected into athymic mice, the 55 kDa C-terminal tagged protein was the predominant species detected as circulating in the mouse blood, when mouse serum is analyzed by serial immunoprecipitation and western blot analysis directed against the V5 tag. The precise location of the cleavage site accounting for the C-terminal fragment was established by excising the acrylamide gel band containing the purified C-terminal fragment and performing mass spectroscopy analysis of tryptic fragments from the protein. A peptide of sequence AVLAAHCPFYSWK (SEQ ID NO: 5) was present only in the digest of the 55 KD fragment, but was absent from the digest of the full length protein, demonstrating that this peptide corresponded to the unique amino terminus of the 55 KD fragment. The complete sequence of the 55 KD C-terminal fragment is shown in FIG. 7.

The sequences of secreted ColoUp2 protein in cell lines derived from other cancer tissues (e.g., endometrium, kidney, lung, stomach, pancreas, breast, prostate, ovary, uterus, and thyroid) can be similarly analyzed.

Example 5

Detecting Expression of ColoUp2 in Various Cancer Types

We describe herein expression of ColoUp2 in an expanded list of human cancers, indicating that ColoUp2 is useful as a diagnostic biomarker (e.g., in blood or other bodily fluids) for cancers with usefulness for early detection of or for monitoring response to therapy of these cancer types.

Figure 8:
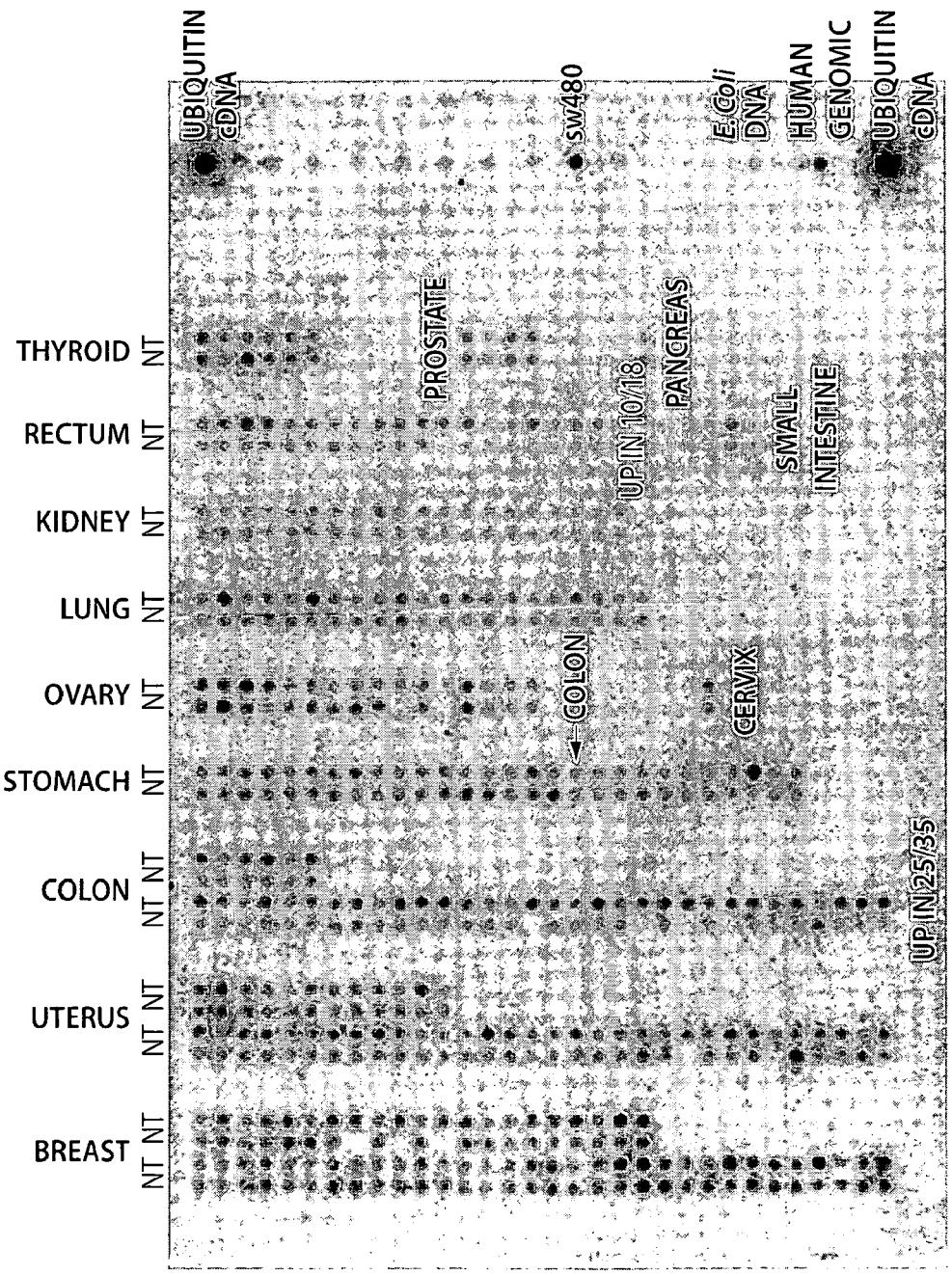
FIG. 8 shows ColoUp2 expression in various cancer types in dot blot experiments.

Initial analysis of ColoUp2 expression across a spectrum of human cancers was done by hybridization of a ColoUp2 cDNA probe to a dot blot membrane containing RNA from cancer tissues and paired normal tissues across a variety of human cancers. The findings of this study are summarized in Table 1. This study detected an increase in ColoUp2 level in 70% of colon cancers and 50% of rectal cancers. The sensitivity of this experiment was limited by the high background on the blot and by the presumed admixture of normal and tumor cells in the cancer specimen. Thus, due to the high background on the blot, the magnitude of the increase in ColoUp2 detected in colon cancer appears much smaller than that we had previously demonstrated by quantitative analysis of ColoUp2 in colon cancers using real-time PCR methods. Nonetheless, using this dot blot approach, we did detect evidence for ColoUp2 induction in a subset clustering around 30% of cases of lung cancer and around 20% of breast cancers and endometrial (uterine) cancers, and 13% of ovarian cancers. An example of the dot blot is shown in FIG. 8.

TABLE 1

A summary of dot blot results showing ColoUp2 expression in various cancers.

| Cancer Type | Number of Samples | Number of ColoUp2 Positive | % Positive Samples |
| --- | --- | --- | --- |
| Colon | 35 | 25 | 71.4 |
| Rectum | 18 | 10 | 55.6 |
| Lung | 21 | 6 | 28.6 |
| Breast | 51 | 10 | 19.6 |
| Uterus | 45 | 8 | 17.8 |
| Ovary | 15 | 2 | 13.3 |
| Kidney | 20 | 0 | 0.0 |
| Thyroid | 6 | 0 | 0.0 |
| Prostate | 4 | 0 | 0.0 |

Figure 9:
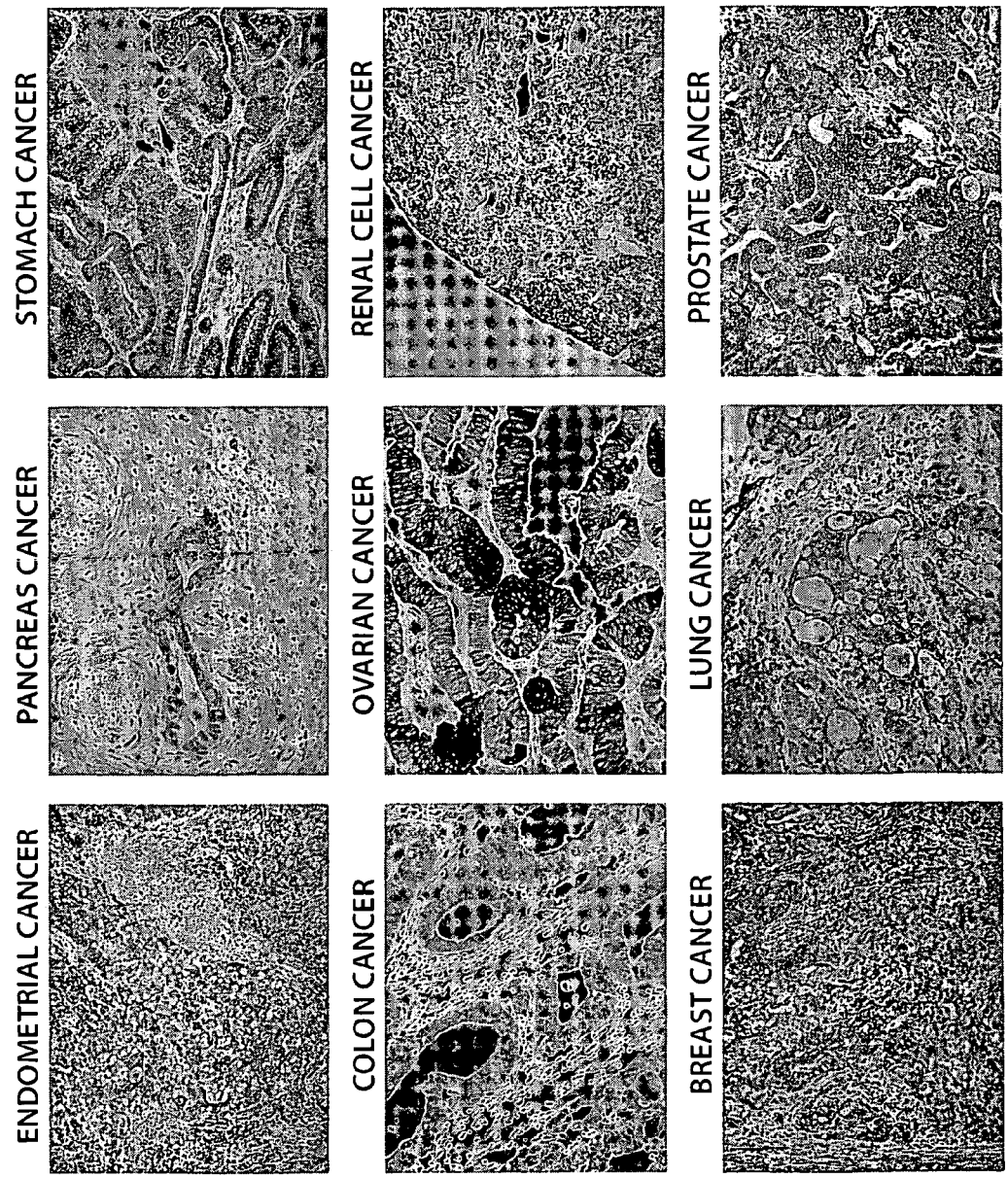
FIG. 9 shows ColoUp2 expression in various cancer types in immuno-histochemical experiments. For example, top left is endometrial cancer, top center is pancreatic cancer, top right is stomach cancer, middle left is colon cancer, middle center is ovarian cancer, middle right is renal cell cancer, bottom left is breast cancer, bottom center is lung cancer, and bottom right is prostate cancer.

To provide better sensitivity for analysis of ColoUp2 expression, we developed an immunohistochemical assay for ColoUp2 protein expression. This assay allows direct visualization of the malignant cells in a tumor sample, and determination of the presence or absence of ColoUp2 protein in the cancer cells. Slices were cut from paraffin blocks of adenocarcinomas from 9 different common cancer types and were stained with an antibody 148-1-1A2-E4-A10 that we have shown by western blot analysis is specific for binding only to ColoUp2 and that we have found has utility for immunohistochemical detection of ColoUp2 in formalin fixed paraffin embedded samples. The results of this study are summarized in Table 2. In particular, the study demonstrated ColoUp2 expression in 100% of endometrial and 95% of renal cancers, a level exceeding even the 75% rate of ColoUp2-positive tumors demonstrated by colon cancers. Thus, detection of ColoUp2 in blood or other bodily fluids may also have utility as a diagnostic biomarker of endometrial or renal cancers, with usefulness for early detection of or for monitoring response to therapy of endometrial or renal cancers. In addition, ColoUp2 expression was detected in 55% of adenocarcinomas of the lung, 42% of gastric cancers, 39% of pancreatic cancers, 22% of prostate cancers, and 18% of ovarian cancers. Thus, in some instances, detection of ColoUp2 in blood or other bodily fluids may also have utility as a diagnostic biomarker of adenocarcinoma of the lung, of gastric cancer, of pancreatic cancer, of prostate cancer, or of ovarian cancer, with usefulness for early detection of or for monitoring response to therapy of certain cases of these cancer types. Photographs of representative immunostained slides of different tumors (with the immunostaining representing ColoUp2 protein) are shown in FIG. 9.

TABLE 2

A summary of immunohistochemical results showing ColoUp2 expression in various cancers.

| Cancer Type | Number of Samples | Number ColoUp2 Positive | % Positive Samples | Minimum % of cells staining in positive cases (defining + as >40%) | Maximum % of cells staining in positive cases |
| --- | --- | --- | --- | --- | --- |
| Endometrium | 12 | 12 | 100.0 | 60% | 100% |
| Renal | 18 | 17 | 94.4 | 70% | 100% |
| Colon | 28 | 21 | 75.0 | 40% | 90% |
| Lung AdenoCA | 20 | 11 | 55.0 | 50% | 90% |
| Gastric | 12 | 5 | 41.7 | 70% | 100% |
| Pancreas | 28 | 11 | 39.3 | 40% | 90% |
| Breast | 22 | 7 | 31.8 | 40% | 100% |
| Prostate | 9 | 2 | 22.2 | 90% | 90% |
| Ovary | 11 | 2 | 18.2 | 60% | 80% |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method for detecting whether a subject has a neoplasia of a tissue type selected from endometrium, kidney, stomach, pancreas, and uterus, comprising:
   (a) selecting a subject from a population, wherein the subject is suspected of harboring a neoplasia of a tissue type selected from endometrium, kidney, stomach, pancreas, and uterus;
   (b) obtaining a biological sample from said subject; and
   (c) detecting in the biological sample a ColoUp2 polypeptide, wherein the ColoUp2 polypeptide is encoded by a nucleic acid sequence that is at least 95% identical to the nucleic acid sequence of SEQ ID NO: 2.

2. The method of claim 1, wherein the ColoUp2 polypeptide is encoded by a nucleic acid sequence that is at least 98% identical to the nucleic acid sequence of SEQ ID NO: 2.

3. The method of claim 1, wherein the ColoUp2 polypeptide is encoded by SEQ ID NO: 2.

4. The method of claim 1, wherein the ColoUp2 polypeptide is encoded by a nucleic acid sequence that hybridizes under stringent conditions to a nucleic acid sequence of SEQ ID NO: 2.

5. The method of claim 1, wherein the ColoUp2 polypeptide has an amino acid sequence that is at least 95% identical to the amino acid sequence as set forth in SEQ ID NO: 1.

6. The method of claim 1, wherein the ColoUp2 polypeptide has an amino acid sequence that is at least 95% identical to the amino acid sequence as set forth in SEQ ID NO: 3.

7. The method of claim 1, wherein said biological sample is selected from whole blood, blood plasma, blood serum, urine, and stool samples.

8. The method of claim 7, wherein said biological sample is a serum sample.

9. The method of claim 8, wherein said serum sample is enriched for ColoUp2.

10. The method of claim 1, wherein the Colo Up2 polypeptide is detected by contacting the biological sample with an antibody that interacts with the ColoUp2 polypeptide.

11. The method of claim 10, wherein the antibody interacts with an epitope on SEQ ID NO: 1 or a portion thereof.

12. The method of claim 11, wherein the antibody is detectably labeled.

13. The method of claim 12, wherein the label is selected from an enzyme, a fluorescent substance, a chemiluminescent substance, a chromophore, a radioactive isotope and a complexing agent.

14. The method of claim 1, further comprising determining the amount of said ColoUp2 polypeptide in the biological sample.

15. The method of claim 1, wherein the presence of the ColoUp2 polypeptide aids in determining a therapeutic protocol to be administered to the subject having said neoplasia.

16. The method of claim 1, wherein said neoplasia is a cancer of a tissue selected from uterus, kidney, stomach, and pancreas.

17. The method of claim 1, wherein said neoplasia is a metastatic cancer initially arising in a tissue selected from uterus, kidney, stomach, and pancreas.

18. The method of claim 1, wherein if ColoUp2 is detected in the biological sample in step (c), said method further comprises surgically removing said neoplasia from said subject.

19. The method of claim 1, wherein if ColoUp2 is detected in the biological sample in step (c), said method further comprises treating said subject with chemotherapy.

20. The method of claim 1, wherein the subject is suspected of harboring a neoplasia of an endometrium tissue type.

21. The method of claim 1, wherein the subject is suspected of harboring a neoplasia of a kidney tissue type.

22. The method of claim 1, wherein the subject is suspected of harboring a neoplasia of a stomach tissue type.

23. The method of claim 1, wherein the subject is suspected of harboring a neoplasia of a pancreas tissue type.

24. The method of claim 1, wherein the subject is suspected of harboring a neoplasia of a uterus tissue type.

* * * * *

SEQUENCE LISTING

<160> NUMBER OF SEQ ID NOS: 5

<210> SEQ ID NO 1
<211> LENGTH: 732
<212> TYPE: PRT
<213> ORGANISM: Homo sapiens

<400> SEQUENCE: 1

```
Leu Gln Glu Val His Val Ser Lys Glu Thr Ile Gly Lys Ile Ser Ala
1               5                   10                  15

Ala Ser Lys Met Met Trp Cys Ser Ala Ala Val Asp Ile Met Phe Leu
            20                  25                  30

Leu Asp Gly Ser Asn Ser Val Gly Lys Gly Ser Phe Glu Arg Ser Lys
        35                  40                  45

His Phe Ala Ile Thr Val Cys Asp Gly Leu Asp Ile Ser Pro Glu Arg
    50                  55                  60

Val Arg Val Gly Ala Phe Gln Phe Ser Ser Thr Pro His Leu Glu Phe
65                  70                  75                  80

Pro Leu Asp Ser Phe Ser Thr Gln Gln Glu Val Lys Ala Arg Ile Lys
                85                  90                  95

Arg Met Val Phe Lys Gly Gly Arg Thr Glu Thr Glu Leu Ala Leu Lys
            100                 105                 110

Tyr Leu Leu His Arg Gly Leu Pro Gly Gly Arg Asn Ala Ser Val Pro
        115                 120                 125

Gln Ile Leu Ile Ile Val Thr Asp Gly Lys Ser Gln Gly Asp Val Ala
    130                 135                 140

Leu Pro Ser Lys Gln Leu Lys Glu Arg Gly Val Thr Val Phe Ala Val
145                 150                 155                 160

Gly Val Arg Phe Pro Arg Trp Glu Glu Leu His Ala Leu Ala Ser Glu
                165                 170                 175

Pro Arg Gly Gln His Val Leu Leu Ala Glu Gln Val Gly Asp Ala Thr
            180                 185                 190

Asn Gly Leu Phe Ser Thr Leu Ser Ser Ser Ala Ile Cys Ser Ser Ala
        195                 200                 205

Thr Pro Asp Cys Arg Val Glu Ala His Pro Cys Glu His Arg Thr Leu
    210                 215                 220

Glu Met Val Arg Glu Phe Ala Gly Asn Ala Pro Cys Trp Arg Gly Ser
225                 230                 235                 240

Arg Arg Thr Leu Ala Val Leu Ala Ala His Cys Pro Tyr Ser Trp
                245                 250                 255

Lys Arg Val Phe Leu Thr His Pro Ala Thr Cys Tyr Arg Thr Thr Cys
            260                 265                 270

Pro Gly Pro Cys Asp Ser Gln Pro Cys Gln Asn Gly Gly Thr Cys Val
        275                 280                 285

Pro Glu Gly Leu Asp Gly Tyr Gln Cys Leu Cys Pro Leu Ala Phe Gly
    290                 295                 300

Gly Glu Ala Asn Cys Ala Leu Lys Leu Ser Leu Glu Cys Arg Val Asp
305                 310                 315                 320

Leu Leu Phe Leu Leu Asp Ser Ser Ala Gly Thr Thr Leu Asp Gly Phe
                325                 330                 335

Leu Arg Ala Lys Val Phe Val Lys Arg Phe Val Arg Ala Val Leu Ser
            340                 345                 350

Glu Asp Ser Arg Ala Arg Val Gly Val Ala Thr Tyr Ser Arg Glu Leu
        355                 360                 365
```

Leu Val Ala Val Pro Val Gly Glu Tyr Gln Asp Val Pro Asp Leu Val
370                 375                 380

Trp Ser Leu Asp Gly Ile Pro Phe Arg Gly Pro Thr Leu Thr Gly
385                 390                 395                 400

Ser Ala Leu Arg Gln Ala Ala Glu Arg Gly Phe Gly Ser Ala Thr Arg
                405                 410                 415

Thr Gly Gln Asp Arg Pro Arg Val Val Leu Leu Thr Glu Ser
                420                 425                 430

His Ser Glu Asp Glu Val Ala Gly Pro Ala Arg His Ala Arg Ala Arg
                435                 440                 445

Glu Leu Leu Leu Leu Gly Val Gly Ser Glu Ala Val Arg Ala Glu Leu
450                 455                 460

Glu Glu Ile Thr Gly Ser Pro Lys His Val Met Val Tyr Ser Asp Pro
465                 470                 475                 480

Gln Asp Leu Phe Asn Gln Ile Pro Glu Leu Gln Gly Lys Leu Cys Ser
                485                 490                 495

Arg Gln Arg Pro Gly Cys Arg Thr Gln Ala Leu Asp Leu Val Phe Met
                500                 505                 510

Leu Asp Thr Ser Ala Ser Val Gly Pro Glu Asn Phe Ala Gln Met Gln
                515                 520                 525

Ser Phe Val Arg Ser Cys Ala Leu Gln Phe Glu Val Asn Pro Asp Val
530                 535                 540

Thr Gln Val Gly Leu Val Tyr Gly Ser Gln Val Gln Thr Ala Phe
545                 550                 555                 560

Gly Leu Asp Thr Lys Pro Thr Arg Ala Ala Met Leu Arg Ala Ile Ser
                565                 570                 575

Gln Ala Pro Tyr Leu Gly Gly Val Gly Ser Ala Gly Thr Ala Leu Leu
                580                 585                 590

His Ile Tyr Asp Lys Val Met Thr Val Gln Arg Gly Ala Arg Pro Gly
                595                 600                 605

Val Pro Lys Ala Val Val Leu Thr Gly Gly Arg Gly Ala Glu Asp
610                 615                 620

Ala Ala Val Pro Ala Gln Lys Leu Arg Asn Asn Gly Ile Ser Val Leu
625                 630                 635                 640

Val Val Gly Val Gly Pro Val Leu Ser Glu Gly Leu Arg Arg Leu Ala
                645                 650                 655

Gly Pro Arg Asp Ser Leu Ile His Val Ala Ala Tyr Ala Asp Leu Arg
                660                 665                 670

Tyr His Gln Asp Val Leu Ile Glu Trp Leu Cys Gly Glu Ala Lys Gln
                675                 680                 685

Pro Val Asn Leu Cys Lys Pro Ser Pro Cys Met Asn Glu Gly Ser Cys
690                 695                 700

Val Leu Gln Asn Gly Ser Tyr Arg Cys Lys Cys Arg Asp Gly Trp Glu
705                 710                 715                 720

Gly Pro His Cys Glu Asn Arg Phe Leu Arg Arg Pro
                725                 730

<210> SEQ ID NO 2
<211> LENGTH: 2810
<212> TYPE: DNA
<213> ORGANISM: Homo sapiens

<400> SEQUENCE: 2 gcccccctggc cgagccgcg cccgggtctg tgagtagagc cgcccgggca ccgagcgctg      60

```
gtcgccgctc tccttccgtt atatcaacat gccccctttc ctgttgctgg aagccgtctg    120
tgttttcctg ttttccagag tgccccatc tctccctctc caggaagtcc atgtaagcaa      180
agaaaccatc gggaagattt cagctgccag caaaatgatg tggtgctcgg ctgcagtgga    240
catcatgttt ctgttagatg gtctaacag cgtcgggaaa gggagctttg aaaggtccaa     300
gcactttgcc atcacagtct gtgacggtct ggacatcagc cccgagaggg tcagagtggg    360
agcattccag ttcagttcca ctcctcatct ggaattcccc ttggattcat tttcaaccca    420
acaggaagtg aaggcaagaa tcaagaggat ggttttcaaa ggagggcgca cggagacgga   480
acttgctctg aaatacttc tgcacagagg gttgcctgga ggcagaaatg cttctgtgcc     540
ccagatcctc atcatcgtca ctgatgggaa gtcccagggg gatgtggcac tgccatccaa    600
gcagctgaag gaaggggtg tcactgtgtt tgctgtgggg gtcaggtttc ccaggtggga     660
ggagctgcat gcactggcca gcgagcctag agggcagcac gtgctgttgg ctgagcaggt    720
ggaggatgcc accaacggcc tcttcagcac cctcagcagc tcggccatct gctccagcgc    780
cacgccagac tgcagggtcg aggctcaccc ctgtgagcac aggacgctgg agatggtccg    840
ggagttcgct ggcaatgccc catgctggag aggatcgcgg cggacccttg cggtgctggc    900
tgcacactgt cccttctaca gctggaagag agtgttccta acccaccctg ccacctgcta    960
caggaccacc tgcccaggcc cctgtgactc gcagccctgc cagaatggag gcacatgtgt   1020
tccagaagga ctggacggct accagtgcct ctgcccgctg gcctttggag gggaggctaa   1080
ctgtgccctg aagctgagcc tggaatgcag ggtcgacctc ctcttcctgc tggacagctc   1140
tgcgggcacc actctggacg gcttcctgcg ggccaaagtc ttcgtgaagc ggtttgtgcg   1200
ggccgtgctg agcgaggact ctcgggcccg agtgggtgtg ccacatacagcagggagct    1260 gctggtggcg gtgcctgtgg gggagtacca ggatgtgcct gacctggtct ggagcctcga   1320
tggcattccc ttccgtggtg gccccaccct gacgggcagt gccttgcggc aggcggcaga   1380
gcgtggcttc gggagcgcca ccaggacagg ccaggaccgg ccacgtagag tggtggtttt   1440
gctcactgag tcacactccg aggatgaggt tgcgggccca gcgcgtcacg caagggcgcg   1500
agagctgctc ctgctgggtg taggcagtga ggccgtgcgg gcagagctgg aggagatcac   1560
aggcagccca aagcatgtga tggtctactc ggatcctcag gatctgttca accaaatccc   1620
tgagctgcag gggaagctgt gcagccggca gcggccaggg tgccggacac aagccctgga   1680
cctcgtcttc atgttggaca cctctgcctc agtagggccc gagaattttg ctcagatgca   1740
gagctttgtg agaagctgtg ccctccagtt tgaggtgaac cctgacgtga cacaggtcgg   1800
cctggtggtg tatggcagcc aggtgcagac tgccttcggg ctggacacca aacccacccg   1860
ggctgcgatg ctgcgggcca ttagccaggc ccccctaccta ggtggggtgg gctcagccgg   1920
caccgccctg ctgcacatct atgacaaagt gatgaccgtc cagaggggtg cccggcctgg    1980
tgtcccccaa gctgtggtgg tgctcacagg cgggagaggc gcagaggatg cagccgttcc   2040
tgcccagaag ctgaggaaca atggcatctc tgtcttggtc gtgggcgtgg ggcctgtcct   2100
aagtgagggt ctgcggaggc ttgcaggtcc ccgggattcc ctgatccacg tggcagctta   2160
cgccgacctg cggtaccacc aggacgtgct cattgagtgg ctgtgtggag aagccaagca   2220
gccagtcaac ctctgcaaac ccagcccgtg catgaatgag ggcagctgcg tcctgcagaa   2280
tgggagctac cgctgcaagt gtcgggatgg ctgggagggc ccccactgcg agaaccgatt   2340
cttgagacgc ccctgaggca catggctccc gtgcaggagg gcagcagccg tacccctccc   2400
agcaactaca gagaaggcct gggcactgaa atggtgccta ccttctggaa tgtctgtgcc   2460
```

```
ccaggtccatt agaatgtctg cttcccgccg tggccaggac cactattctc actgagggag    2520
gaggatgtcc caactgcagc catgctgctt agagacaaga aagcagctga tgtcacccac    2580
aaacgatgtt gttgaaaagt tttgatgtgt aagtaaatac ccactttctg tacctgctgt    2640
gccttgttga ggctatgtca tctgccacct ttcccttgag gataaacaag gggtcctgaa    2700
gacttaaatt tagcggcctg acgttccttt gcacacaatc aatgctcgcc agaatgttgt    2760
tgacacagta atgcccagca gaggccttta ctagagcatc ctttggacgg               2810
```

<210> SEQ ID NO 3
<211> LENGTH: 755
<212> TYPE: PRT
<213> ORGANISM: Homo sapiens
<400> SEQUENCE: 3

```
Met Pro Pro Phe Leu Leu Leu Glu Ala Val Cys Val Phe Leu Phe Ser
1               5                   10                  15

Arg Val Pro Pro Ser Leu Pro Leu Gln Glu Val His Val Ser Lys Glu
            20                  25                  30

Thr Ile Gly Lys Ile Ser Ala Ala Ser Lys Met Met Trp Cys Ser Ala
        35                  40                  45

Ala Val Asp Ile Met Phe Leu Leu Asp Gly Ser Asn Ser Val Gly Lys
    50                  55                  60

Gly Ser Phe Glu Arg Ser Lys His Phe Ala Ile Thr Val Cys Asp Gly
65                  70                  75                  80

Leu Asp Ile Ser Pro Glu Arg Val Arg Val Gly Ala Phe Gln Phe Ser
                85                  90                  95

Ser Thr Pro His Leu Glu Phe Pro Leu Asp Ser Phe Ser Thr Gln Gln
            100                 105                 110

Glu Val Lys Ala Arg Ile Lys Arg Met Val Phe Lys Gly Gly Arg Thr
        115                 120                 125

Glu Thr Glu Leu Ala Leu Lys Tyr Leu Leu His Arg Gly Leu Pro Gly
    130                 135                 140

Gly Arg Asn Ala Ser Val Pro Gln Ile Leu Ile Ile Val Thr Asp Gly
145                 150                 155                 160

Lys Ser Gln Gly Asp Val Ala Leu Pro Ser Lys Gln Leu Lys Glu Arg
                165                 170                 175

Gly Val Thr Val Phe Ala Val Gly Val Arg Phe Pro Arg Trp Glu Glu
            180                 185                 190

Leu His Ala Leu Ala Ser Glu Pro Arg Gly Gln His Val Leu Leu Ala
        195                 200                 205

Glu Gln Val Glu Asp Ala Thr Asn Gly Leu Phe Ser Thr Leu Ser Ser
    210                 215                 220

Ser Ala Ile Cys Ser Ser Ala Thr Pro Asp Cys Arg Val Glu Ala His
225                 230                 235                 240

Pro Cys Glu His Arg Thr Leu Glu Met Val Arg Glu Phe Ala Gly Asn
                245                 250                 255

Ala Pro Cys Trp Arg Gly Ser Arg Arg Thr Leu Ala Val Leu Ala Ala
            260                 265                 270

His Cys Pro Phe Tyr Ser Trp Lys Arg Val Phe Leu Thr His Pro Ala
        275                 280                 285

Thr Cys Tyr Arg Thr Thr Cys Pro Gly Pro Cys Asp Ser Gln Pro Cys
    290                 295                 300

Gln Asn Gly Gly Thr Cys Val Pro Glu Gly Leu Asp Gly Tyr Gln Cys
```

```
            305                 310                 315                 320
        Leu Cys Pro Leu Ala Phe Gly Gly Glu Ala Asn Cys Ala Leu Lys Leu
                        325                 330                 335

Ser Leu Glu Cys Arg Val Asp Leu Leu Phe Leu Leu Asp Ser Ser Ala
                        340                 345                 350

Gly Thr Thr Leu Asp Gly Phe Leu Arg Ala Lys Val Phe Val Lys Arg
                        355                 360                 365

Phe Val Arg Ala Val Leu Ser Glu Asp Ser Arg Ala Arg Val Gly Val
        370                 375                 380

Ala Thr Tyr Ser Arg Glu Leu Leu Val Ala Val Pro Val Gly Glu Tyr
        385                 390                 395                 400

Gln Asp Val Pro Asp Leu Val Trp Ser Leu Asp Gly Ile Pro Phe Arg
                        405                 410                 415

Gly Gly Pro Thr Leu Thr Gly Ser Ala Leu Arg Gln Ala Ala Glu Arg
                        420                 425                 430

Gly Phe Gly Ser Ala Thr Arg Thr Gly Gln Asp Arg Pro Arg Arg Val
                        435                 440                 445

Val Val Leu Leu Thr Glu Ser His Ser Glu Asp Glu Val Ala Gly Pro
        450                 455                 460

Ala Arg His Ala Arg Ala Arg Glu Leu Leu Leu Leu Gly Val Gly Ser
        465                 470                 475                 480

Glu Ala Val Arg Ala Glu Leu Glu Glu Ile Thr Gly Ser Pro Lys His
                        485                 490                 495

Val Met Val Tyr Ser Asp Pro Gln Asp Leu Phe Asn Gln Ile Pro Glu
                        500                 505                 510

Leu Gln Gly Lys Leu Cys Ser Arg Gln Arg Pro Gly Cys Arg Thr Gln
                        515                 520                 525

Ala Leu Asp Leu Val Phe Met Leu Asp Thr Ser Ala Ser Val Gly Pro
                        530                 535                 540

Glu Asn Phe Ala Gln Met Gln Ser Phe Val Arg Ser Cys Ala Leu Gln
        545                 550                 555                 560

Phe Glu Val Asn Pro Asp Val Thr Gln Val Gly Leu Val Val Tyr Gly
                        565                 570                 575

Ser Gln Val Gln Thr Ala Phe Gly Leu Asp Thr Lys Pro Thr Arg Ala
                        580                 585                 590

Ala Met Leu Arg Ala Ile Ser Gln Ala Pro Tyr Leu Gly Gly Val Gly
                        595                 600                 605

Ser Ala Gly Thr Ala Leu Leu His Ile Tyr Asp Lys Val Met Thr Val
        610                 615                 620

Gln Arg Gly Ala Arg Pro Gly Val Pro Lys Ala Val Val Leu Leu Thr
        625                 630                 635                 640

Gly Gly Arg Gly Ala Glu Asp Ala Ala Val Pro Ala Gln Lys Leu Arg
                        645                 650                 655

Asn Asn Gly Ile Ser Val Leu Val Val Gly Val Gly Pro Val Leu Ser
                        660                 665                 670

Glu Gly Leu Arg Arg Leu Ala Gly Pro Arg Asp Ser Leu Ile His Val
                        675                 680                 685

Ala Ala Tyr Ala Asp Leu Arg Tyr His Gln Asp Val Leu Ile Glu Trp
        690                 695                 700

Leu Cys Gly Glu Ala Lys Gln Pro Val Asn Leu Cys Lys Pro Ser Pro
        705                 710                 715                 720

Cys Met Asn Glu Gly Ser Cys Val Leu Gln Asn Gly Ser Tyr Arg Cys
                        725                 730                 735
```

```
Lys Cys Arg Asp Gly Trp Glu Gly Pro His Cys Glu Asn Arg Phe Leu
                740                 745                 750
Arg Arg Pro
        755

<210> SEQ ID NO 4
<211> LENGTH: 488
<212> TYPE: PRT
<213> ORGANISM: Homo sapiens

<400> SEQUENCE: 4

Ala Val Leu Ala Ala His Cys Pro Phe Tyr Ser Trp Lys Arg Val Phe
1               5                   10                  15

Leu Thr His Pro Ala Thr Cys Tyr Arg Thr Thr Cys Pro Gly Pro Cys
            20                  25                  30

Asp Ser Gln Pro Cys Gln Asn Gly Gly Thr Cys Val Pro Glu Gly Leu
        35                  40                  45

Asp Gly Tyr Gln Cys Leu Cys Pro Leu Ala Phe Gly Gly Glu Ala Asn
    50                  55                  60

Cys Ala Leu Lys Leu Ser Leu Glu Cys Arg Val Asp Leu Leu Phe Leu
65                  70                  75                  80

Leu Asp Ser Ser Ala Gly Thr Thr Leu Asp Gly Phe Leu Arg Ala Lys
                85                  90                  95

Val Phe Val Lys Arg Phe Val Arg Ala Val Leu Ser Glu Asp Ser Arg
            100                 105                 110

Ala Arg Val Gly Val Ala Thr Tyr Ser Arg Glu Leu Leu Val Ala Val
        115                 120                 125

Pro Val Gly Glu Tyr Gln Asp Val Pro Asp Leu Val Trp Ser Leu Asp
    130                 135                 140

Gly Ile Pro Phe Arg Gly Gly Pro Thr Leu Thr Gly Ser Ala Leu Arg
145                 150                 155                 160

Gln Ala Ala Glu Arg Gly Phe Gly Ser Ala Thr Arg Thr Gly Gln Asp
                165                 170                 175

Arg Pro Arg Arg Val Val Val Leu Leu Thr Glu Ser His Ser Glu Asp
            180                 185                 190

Glu Val Ala Gly Pro Ala Arg His Ala Arg Ala Arg Glu Leu Leu Leu
        195                 200                 205

Leu Gly Val Gly Ser Glu Ala Val Arg Ala Glu Leu Glu Glu Ile Thr
    210                 215                 220

Gly Ser Pro Lys His Val Met Val Tyr Ser Asp Pro Gln Asp Leu Phe
225                 230                 235                 240

Asn Gln Ile Pro Glu Leu Gln Gly Lys Leu Cys Ser Arg Gln Arg Pro
                245                 250                 255

Gly Cys Arg Thr Gln Ala Leu Asp Leu Val Phe Met Leu Asp Thr Ser
            260                 265                 270

Ala Ser Val Gly Pro Glu Asn Phe Ala Gln Met Gln Ser Phe Val Arg
        275                 280                 285

Ser Cys Ala Leu Gln Phe Glu Val Asn Pro Asp Val Thr Gln Val Gly
    290                 295                 300

Leu Val Val Tyr Gly Ser Gln Val Gln Thr Ala Phe Gly Leu Asp Thr
305                 310                 315                 320

Lys Pro Thr Arg Ala Ala Met Leu Arg Ala Ile Ser Gln Ala Pro Tyr
                325                 330                 335

Leu Gly Gly Val Gly Ser Ala Gly Thr Ala Leu Leu His Ile Tyr Asp
```

-continued

```
                        340                 345                 350
Lys Val Met Thr Val Gln Arg Gly Ala Arg Pro Gly Val Pro Lys Ala
            355                 360                 365

Val Val Val Leu Thr Gly Gly Arg Gly Ala Glu Asp Ala Ala Val Pro
        370                 375                 380

Ala Gln Lys Leu Arg Asn Asn Gly Ile Ser Val Leu Val Val Gly Val
385                 390                 395                 400

Gly Pro Val Leu Ser Glu Gly Leu Arg Arg Leu Ala Gly Pro Arg Asp
                405                 410                 415

Ser Leu Ile His Val Ala Ala Tyr Ala Asp Leu Arg Tyr His Gln Asp
                420                 425                 430

Val Leu Ile Glu Trp Leu Cys Gly Glu Ala Lys Gln Pro Val Asn Leu
            435                 440                 445

Cys Lys Pro Ser Pro Cys Met Asn Glu Gly Ser Cys Val Leu Gln Asn
        450                 455                 460

Gly Ser Tyr Arg Cys Lys Cys Arg Asp Gly Trp Glu Gly Pro His Cys
465                 470                 475                 480

Glu Asn Arg Phe Leu Arg Arg Pro
                485

<210> SEQ ID NO 5
<211> LENGTH: 13
<212> TYPE: PRT
<213> ORGANISM: Homo sapiens

<400> SEQUENCE: 5

Ala Val Leu Ala Ala His Cys Pro Phe Tyr Ser Trp Lys
1               5                   10
```